(12) United States Patent
Ohnishi et al.

(10) Patent No.: US 8,100,013 B2
(45) Date of Patent: Jan. 24, 2012

(54) PASSAGE DETECTION APPARATUS OF OBJECT

(75) Inventors: Takao Ohnishi, Nagoya (JP); Kunihiko Yoshioka, Nagoya (JP); Shuhei Fujita, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 12/710,577

(22) Filed: Feb. 23, 2010

(65) Prior Publication Data

US 2010/0148803 A1  Jun. 17, 2010

Related U.S. Application Data

(60) Division of application No. 11/947,120, filed on Nov. 29, 2007, now Pat. No. 7,707,887, which is a continuation of application No. PCT/JP2006/311149, filed on May 29, 2006.

(30) Foreign Application Priority Data

May 31, 2005  (JP) ................... 2005-159768

(51) Int. Cl.
  *G01H 5/00*  (2006.01)
(52) U.S. Cl. ........... 73/597; 73/579; 73/861.14; 367/93; 367/95
(58) Field of Classification Search ............ 73/579, 73/597, 861.14; 367/93, 95
See application file for complete search history.

(56) References Cited

U.S. PATENT DOCUMENTS

| | | | |
|---|---|---|---|
| 2,826,753 A | 3/1958 | Chapin | |
| 3,065,455 A | 11/1962 | Roth | |
| 3,881,353 A | 5/1975 | Fathauer | |
| 3,974,681 A | 8/1976 | Namery | |
| 4,335,617 A | 6/1982 | Ashmore et al. | |
| 4,473,822 A | 9/1984 | Schiffl | |
| 4,617,608 A * | 10/1986 | Blonder et al. | 361/291 |
| 4,887,248 A * | 12/1989 | Griebeler | 367/181 |
| 5,768,937 A * | 6/1998 | Wajid et al. | 73/24.06 |
| 5,801,313 A * | 9/1998 | Horibata et al. | 73/718 |
| 6,075,867 A * | 6/2000 | Bay et al. | 381/191 |
| 6,094,987 A | 8/2000 | Suzuki et al. | |
| 6,272,916 B1 | 8/2001 | Taniguchi et al. | |
| 6,365,378 B1 | 4/2002 | Hirota et al. | |
| 7,107,852 B2 * | 9/2006 | Hutchins et al. | 73/598 |

FOREIGN PATENT DOCUMENTS

| | | |
|---|---|---|
| DE | 40 34 333 A1 | 12/1991 |
| JP | 58-106774 U1 | 7/1983 |
| JP | 04-004288 U1 | 1/1992 |
| JP | 09-318657 A1 | 12/1997 |
| JP | 2000-121742 A1 | 4/2000 |

(Continued)

*Primary Examiner* — Hezron E Williams
*Assistant Examiner* — Rose M Miller
(74) *Attorney, Agent, or Firm* — Burr & Brown

(57) ABSTRACT

A passage detection apparatus is configured to detect the change in the properties (propagation state of sound wave, dielectric constant, etc.) of a specific space, which changes according to the passage of an object in the specific space and the size of the object. The passage detection apparatus includes a pair of detection units and configured to transmit and receive signals to and from an external device. The specific space is formed by the space between the detection unit and the detection unit. The detection unit is supported by a first substrate. The detection unit is supported by a second substrate that is parallel to the first substrate, and arranged at the position corresponding to the detection unit supported by the first substrate.

2 Claims, 24 Drawing Sheets

FOREIGN PATENT DOCUMENTS

| | | |
|---|---|---|
| JP | 2001-124789 A1 | 5/2001 |
| JP | 2001-186881 A1 | 7/2001 |
| JP | 2001-255381 A1 | 9/2001 |
| JP | 2002-341047 A1 | 11/2002 |

* cited by examiner

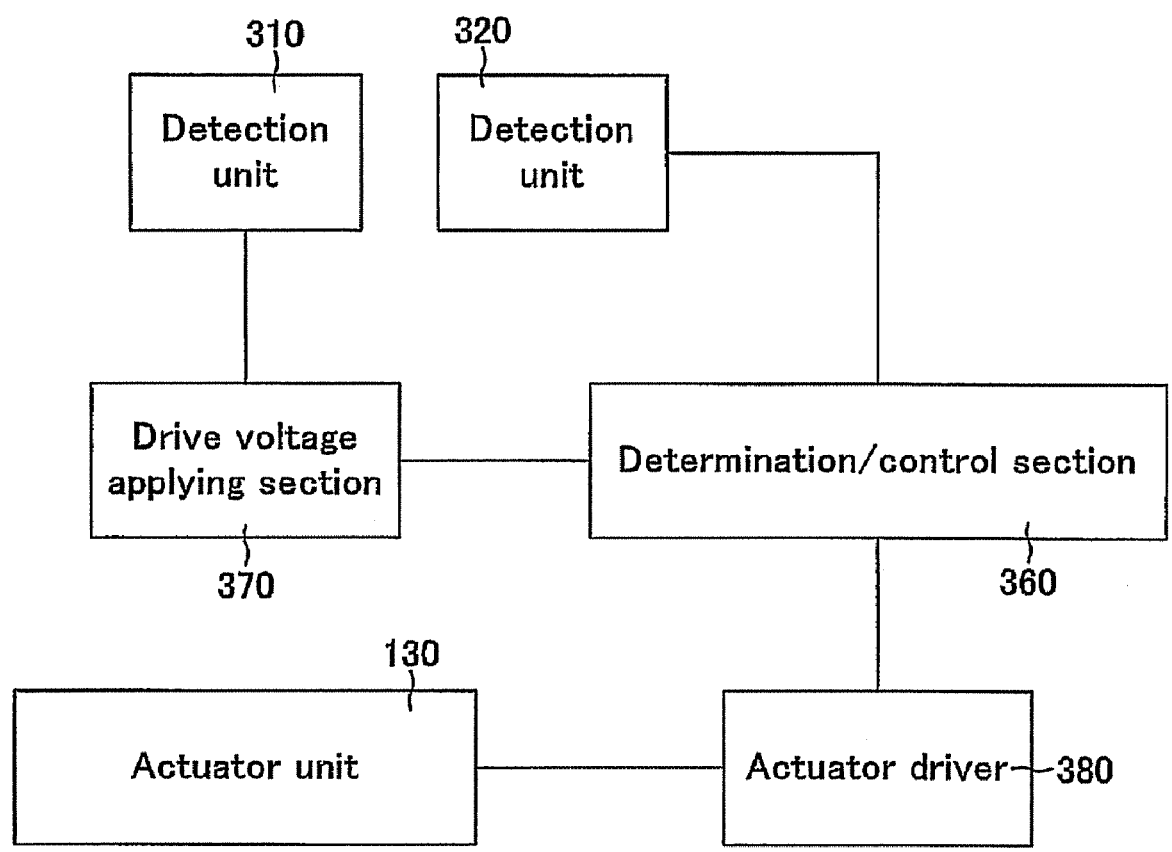

FIG. 19
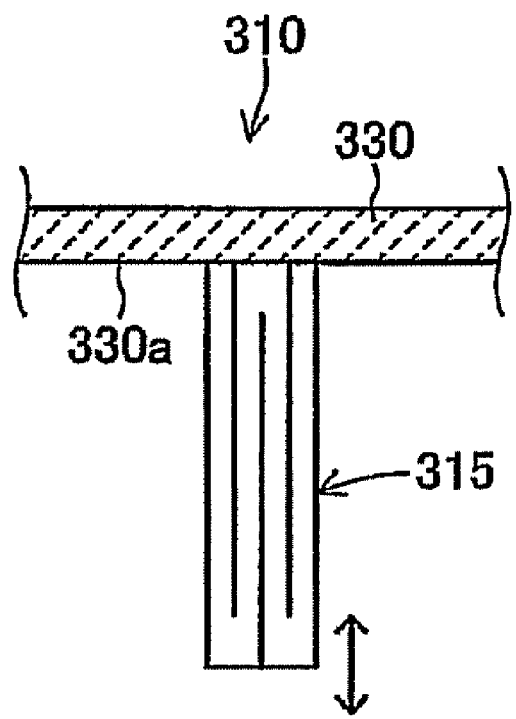
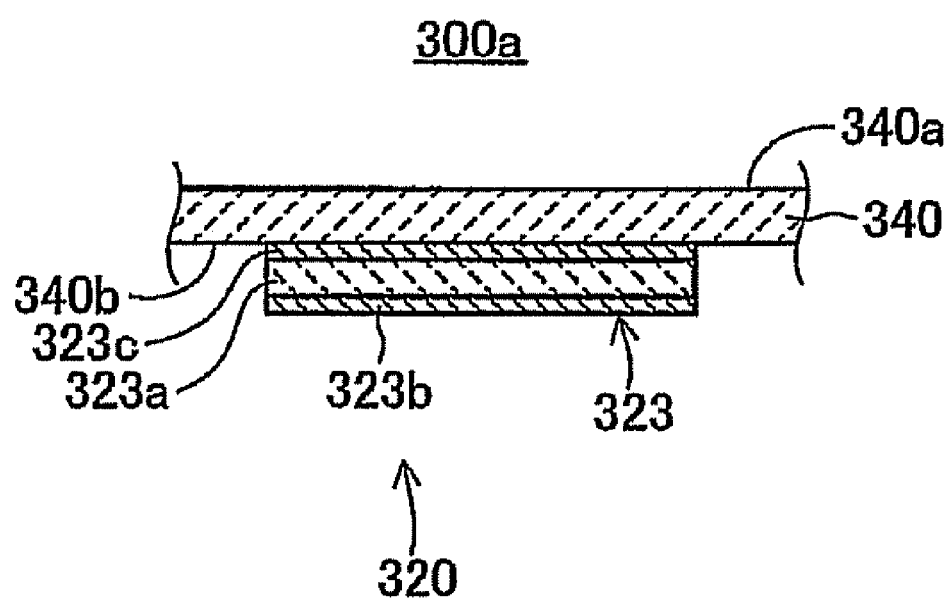

PASSAGE DETECTION APPARATUS OF OBJECT

CROSS REFERENCE TO RELATED APPLICATIONS

This application is a division of U.S. application Ser. No. 11/947,120, filed Nov. 29, 2007, which in turn is a continuation of International Application No. PCT/JP2006/311149, filed May 29, 2006, which designated the United States, and claims the benefit under 35 USC §119(a)-(d) of Japanese Application No. 2005-159768, filed May 31, 2005, the entireties of which are incorporated herein by reference.

FIELD OF THE INVENTION

The present invention relates to a passage detection apparatus of an object that can detect a passage of the object in a specific space.

BACKGROUND OF THE INVENTION

For example, various methods of manufacturing a so-called DNA chip (a DNA micro array) are well known. The DNA chip is generally constructed by arraying and fixing micro spots of several thousand to ten thousand or more kinds of different DNA pieces on a substrate, such as a microscope slide glass, with high density.

As examples of the DNA chip manufacturing methods, there have been proposed methods of manufacturing a DNA chip using a micropipette for ejecting drops having micro volume (for example, Japanese Patent Application Laid-Open (Kokai) Nos. 2001-124789 and 2001-186881). The micropipette includes an injection port for injecting a sample solution from the outside, a cavity for allowing the sample solution injected from the injection port to be filled therein, an ejection port communicating with the cavity, and a piezoelectric/electrostrictive element constructed to change the interior volume of the cavity such that the sample solution can be ejected from the ejection port.

According to the above-described DNA chip manufacturing methods, the interior volume of the cavity is changed by the driving operation of the piezoelectric/electrostrictive element. As the interior volume of the cavity is changed, the sample solution moves from the cavity to the ejection port in the form of a streamline flow. That is, a predetermined amount of the sample solution is delivered from the cavity to the ejection port. As the predetermined amount of the sample solution is ejected from the ejection port, micro drops of the sample solution are generated. The micro drops of the sample solution ejected from the micropipette are attached to the substrate, and the micro drops are arrayed and fixed on the substrate as micro spots. In this way, the DNA chip is manufactured.

An apparatus constructed to eject a micro object (hereinafter, simply referred to as a "micro object ejection apparatus"), such as the micropipette used in the DNA chip manufacturing method as described above, may be utilized in various technical fields.

SUMMARY OF THE INVENTION

In this kind of micro object ejection apparatus, the dried and hardened portion of the micro object or foreign matter might be attached around the ejection port, and as a result, the ejection port may be obstructed. In this case, the micro object may not be accurately ejected toward a predetermined position to which the micro object is to be ejected (for example, see columns [0010] and [0019] of Japanese Patent Application Laid-Open (Kokai) No. 2001-124789).

Therefore, the present invention has been made in view of the above problems, and it is an object of the present invention to provide a passage detection apparatus of an object that is capable of detecting the passage of the micro object in a specific space through which the micro object should pass when the micro object is ejected, in order to grasp the ejection state of the micro object in the micro object ejection apparatus, the passage detection apparatus of an object being manufactured in a simplified structure and at low costs.

Configuration A: Sonic Type

In order to achieve the foregoing object, the passage detection apparatus of an object (hereinafter simply referred to as "passage detection apparatus") includes the following configurations.

A01

The passage detection apparatus according to the present invention includes a vibration generating source, a sensor unit, and a determination unit. The vibration generating source is configured to be capable of generating vibration that is propagated in the specific space. Ultrasonic wave is preferable for the vibration. The sensor unit is arranged at the position corresponding to the vibration generating source across the specific space, and is configured to be capable of generating an output according to the vibration propagating via a medium in the specific space. The determination unit is configured to determine the passage of the object in the specific space on the basis of the output from the sensor unit.

In the configuration described above, the propagation state of the vibration at the medium (e.g., air) in the specific space changes depending upon the presence of the object. Accordingly, the determination unit can determine whether the object passes or not in the specific space on the basis of the change in the output (e.g., output voltage) by the sensor unit, for example. The propagation state at the medium (e.g., air) in the specific space also changes according to the size of the object. Therefore, the determination unit can also determine the size of the object.

A02

In the above-mentioned configuration A01, the vibration generating source and the sensor unit may be comprised of a piezoelectric/electrostrictive element. Specifically, the vibration generating source is comprised of a first piezoelectric/electrostrictive element having a first dielectric layer, and a drive electrode and a first reference electrode that are formed at both sides of the first dielectric layer. The sensor unit is comprised of a second piezoelectric/electrostrictive element having a second dielectric layer, and a signal output electrode and a second reference electrode that are formed at both sides of the second dielectric layer.

In this configuration, since a drive voltage is applied between the first reference electrode and the drive electrode, the vibration is generated from the first piezoelectric/electrostrictive element on the basis of the inverse piezoelectric effect. This vibration is propagated to the second piezoelectric/electrostrictive element through the medium. By this vibration, the output voltage is generated between the second reference electrode and the signal output electrode on the basis of the piezoelectric effect. The determination unit determines whether the object passes in the specific space or not and/or determines the size of the object on the basis of the output voltage. According to this configuration, whether the object passes or not in the specific space and/or the size of the object can surely be determined with simple structure, regardless of the conductivity of the object.

A03

In the above-mentioned configuration A02, the vibration generating source and the sensor unit may be arranged such that the first reference electrode and the second reference electrode are arranged at the side close to the specific space. In this case, the passage detection apparatus is configured such that the first reference electrode and the second reference electrode arranged at both side of the specific space so as to face the specific space have the same potential. Alternatively, the passage detection apparatus is configured such that the first reference electrode and the second reference electrode have different potential.

When the first reference electrode and the second reference electrode, which are arranged at both sides of the specific space so as to face the specific space, have the same potential (e.g., when the first reference electrode and the second reference electrode are both grounded), the electric field intensity between the first reference electrode and the second reference electrode becomes nearly zero. Therefore, when the object is electrostatically charged (e.g., in cases where the object is a water-based micro drop), it can be prevented that the flight route of the object is curved by moving the object toward the side of the first reference electrode or the second reference electrode during the passage in the specific space. Accordingly, even when the object is electrostatically charged, the passage of the object or the size of the object can satisfactorily be determined.

When a potential difference is formed between the first reference electrode and the second reference electrode arranged at both sides of the specific space so as to face the specific space, the detection sensitivity of the passage of the object in the specific space is further enhanced. Specifically, electrostatic capacity changes in the specific space depending upon whether the object passes through the specific space or not or depending upon the property of the object. The above-mentioned potential difference (voltage) can be varied on the basis of the change in the electrostatic capacity. The use of the variation in the voltage and the change in the vibration propagation state makes it possible to detect the passage of the object in the specific space or the property of the object with higher sensitivity (the operation and effect same as those achieved by the later-described configuration in D01 can be provided).

A04

In the configurations A02 and A03, a first substrate made of a plate-like dielectric layer and supporting the first piezoelectric/electrostrictive element and a second substrate made of a plate-like dielectric layer and supporting the second piezoelectric/electrostrictive element may be further provided. In this case, the specific space is formed from a space between the first substrate and the second substrate. Ceramic or the like is preferably used, for example, as the dielectric layer composing the first substrate and the second substrate.

According to the configuration described above, the first piezoelectric/electrostrictive element and the second piezoelectric/electrostrictive element are surely be supported by the first substrate and the second substrate. Therefore, the vibration toward the medium from the first piezoelectric/electrostrictive element can more efficiently be propagated. Further, the vibration from the medium can more efficiently be received by the second piezoelectric/electrostrictive element. Moreover, the specific space that has the microstructure and through which the object passes can surely be formed to have a desired shape and size.

A05

In the above-mentioned configuration A04, the first piezoelectric/electrostrictive element may be held on an inner surface, which is the surface at the side of the specific space, of the first substrate, and the second piezoelectric/electrostrictive element may be held on an inner surface, which is the surface at the side of the specific space, of the second substrate. Specifically, the first piezoelectric/electrostrictive element and the second piezoelectric/electrostrictive element may be arranged so as to face the specific space.

In the configuration described above, the space between the first piezoelectric/electrostrictive element and the second piezoelectric/electrostrictive element forms the specific space. The vibration is propagated to the second piezoelectric/electrostrictive element from the first piezoelectric/electrostrictive element through the medium in the specific space. Accordingly, the passage of the object and/or the size of the object can be determined with excellent sensitivity by a simplified structure.

A06

In the above-mentioned configuration A04, the first piezoelectric/electrostrictive element may be held on an outer surface, which is the surface reverse to an inner surface at the side of the specific space, of the first substrate, and the second piezoelectric/electrostrictive element may be held on an outer surface, which is the surface reverse to an inner surface at the side of the specific space, of the second substrate.

In the configuration described above, the first substrate and the second substrate are arranged in such a manner that the inner surfaces of the first substrate and the second substrate face the specific space (in such a manner that the first piezoelectric/electrostrictive element and the second piezoelectric/electrostrictive element are not exposed to the specific space). Thus, the passage of the object and/or the size of the object can satisfactorily be determined, even when the object is liquid or conductive. It is to be noted that the inner surfaces of the first substrate and the second substrate may be exposed to the specific space, or a coating layer made of an insulating material may be formed on the inner surfaces.

A07

In the above-mentioned configuration A05, a coating layer made of an insulating material may be formed so as to cover the first piezoelectric/electrostrictive element and the second piezoelectric/electrostrictive element.

According to this configuration, a stable performance can be obtained, even if the passage detection apparatus is used under high-humid environment.

When the first piezoelectric/electrostrictive element and the second piezoelectric/electrostrictive element are arranged so as to face the specific space and the object is liquid or conductive, the object is prevented from being directly deposited onto the first piezoelectric/electrostrictive element or the second piezoelectric/electrostrictive element. Accordingly, the occurrence of short-circuit between the first reference electrode and the drive electrode can be prevented. Further, the occurrence of short-circuit between the second reference electrode and the signal output electrode can be prevented. Accordingly, the passage of the object and/or the size of the object can satisfactorily be determined, even when the object is liquid or conductive.

A08

In the above-mentioned configurations A04 to A06, the first substrate and the second substrate may be arranged such that the distance L in the widthwise direction of the specific space (the direction perpendicular to the moving direction of the object and the direction forming the shortest distance between the first substrate and the second substrate) satisfies the equation of L=nλ, or L=(m/2)·λ, wherein the wavelength of the vibration propagating through the medium is defined as λ, and n and m are defined as a natural number. In particular, in the above-mentioned configuration A05, the first substrate and the second substrate may be arranged in such a manner that the distance between the inner surface of the first substrate and the inner surface of the second substrate becomes the distance L. Accordingly, the vibration from the first piezoelectric/electrostrictive element to the second piezoelectric/electrostrictive element can more efficiently be propagated.

A09

In the above-mentioned configurations A04 to A08, the first substrate may include a plate-like thin part and a plate-like thick part that is formed at both sides of the thin part and is thicker than the thin part, wherein the first piezoelectric/electrostrictive element may be attached to the thin part of the first substrate.

In the above-mentioned configuration, the first substrate is formed in such a manner that the thin part is bridged between the adjacent thick parts. Therefore, the vibration can be generated from the first piezoelectric/electrostrictive element, serving as the vibration generating source, with high output.

It is to be noted that the thin part and thick part may be integrally formed from the same material. Alternatively, the thin part is made of a material different from the material of the thick part. In this case, the thin part may be integrally formed with the thick part with a sintering or the like, or may be fixed to the thick part by bonding or welding.

A10

In the above-mentioned configuration A09, the first substrate may be formed such that an outer surface of the thin part and an outer surface of the thick part are continuous on a same plane, and the specific space may be formed to include a space enclosed by an inner surface of the thin part at the first substrate and a side face of the thick part at the first substrate.

In the configuration described above, a concave part composing the specific space is formed at the inner side (the side facing the specific space) of the first substrate, and the thin part is formed so as to be bridged between the adjacent thick parts at the outer side of the first substrate. Therefore, a part of the specific space can be formed within the range of the thickness of the first substrate. Accordingly, the passage detection apparatus can be miniaturized.

A11

In the above-mentioned configuration A10, the side face of the thick part at the first substrate may be configured to be capable of reflecting sound wave or ultrasonic wave.

In the configuration described above, sound wave or ultrasonic wave can be reflected with high efficiency by the inner wall surface of the concave part forming the specific space. Therefore, directivity when the ultrasonic wave or the like propagates through the medium is enhanced. Accordingly, the passage of the object or the like can satisfactorily be detected even though the input voltage in the first piezoelectric/electrostrictive element, which serves as the vibration generating source, is reduced to decrease the power consumption.

A12

In the above-mentioned configurations A04 to A11, the second substrate may include a thin part and a thick part, and the sensor unit and the second electrode may be attached to the thin part of the second substrate. The thin part is formed into a flat plate shape. The thick part is a member having a flat plate shape thicker than the thin part. The thick part is formed at both sides of the thin part.

According to the configuration described above, the second substrate is formed in such a manner that the thin part is bridged between the adjacent thick parts. Therefore, the thin part can be vibrated with high efficiency by the vibration propagating through the medium. Accordingly, the passage of the object or the like can be detected with high sensitivity.

A13

In the above-mentioned configuration A12, the second substrate may be formed such that an outer surface of the thin part and an outer surface of the thick part are continuous on a same plane, and the specific space may be configured to include a space enclosed by an inner surface of the thin part at the second substrate and a side face of the thick part at the second substrate.

In the configuration described above, a concave part composing the specific space is formed at the inner side (the side facing the specific space) of the second substrate, and the thin part is formed so as to be bridged between the adjacent thick parts at the outer side of the second substrate. Therefore, a part of the specific space can be formed within the range of the thickness of the second substrate. Accordingly, the passage detection apparatus can be miniaturized. In particular, nearly entire specific space can be formed within the range of the thickness obtained by superimposing the first and second substrates by the configuration in which the first substrate is foamed in the same manner as the second substrate (refer to the configuration A09). Therefore, the passage detection apparatus can further be miniaturized.

A14

In the above-mentioned configuration A13, the side face of the thick part at the second substrate may be formed to be smooth to an extent of being capable of nearly totally reflecting sound wave or ultrasonic wave.

In the configuration described above, sound wave or ultrasonic wave can be reflected with high efficiency by the inner wall surface of the concave part composing the specific space. Therefore, directivity when the ultrasonic wave or the like propagates through the medium is enhanced. Accordingly, the thin part can be vibrated with high efficiency by the vibration propagating through the medium. In particular, it is preferable that the first substrate is formed in the same manner as the second substrate (refer to the configuration A10). Accordingly, the vibration from the first piezoelectric/electrostrictive element to the second piezoelectric/electrostrictive element in the specific space formed at the inner side of the portion where the first and the second substrates are superimposed can be propagated with high directivity.

A15

In any one of the above-mentioned configurations A04 to A14 the first substrate and the first piezoelectric/electrostrictive element may be integrally formed by sintering, and the second substrate and the second piezoelectric/electrostrictive element may be integrally formed by sintering. Accordingly, the fixing force between each substrate to the corresponding piezoelectric/electrostrictive element is enhanced. Consequently, a passage detection apparatus having high durability can be obtained by a simple manufacturing process.

A16

In any one of the above-mentioned configurations A01 to A15, the vibration generating source may be comprised of a piezoelectric/electrostrictive element having a multi-layer structure.

According to the configuration described above, the output of the vibration from the vibration generating source can be more increased. Therefore, the passage of the object and/or the size of the object can satisfactorily be detected.

Configuration B: Sonic Type/Electrostatic Microphone Sensor Unit

The passage detection apparatus having the configuration A01 may be configured as follows.

B01

The sensor unit includes a vibration plate, a first detection electrode, a support plate, and a second detection electrode. The vibration plate is made of a plate-like dielectric layer. The vibration plate is a member composing the outer wall enclosing the specific space. The first detection electrode is mounted to the vibration plate. The support plate is arranged parallel to the vibration plate with a predetermined gap. The second detection electrode is formed on an inner surface of the support plate opposite to the vibration plate, and is arranged parallel to the first detection electrode. The determination unit is configured to be capable of determining the passage of the object in the specific space on the basis of an electrostatic capacitance between the first detection electrode and the second detection electrode.

In the configuration described above, the propagation state of the vibration of the medium toward the vibration plate in the specific space changes depending upon the presence of the object or the size of the object. Therefore, the vibration state of the vibration plate changes according to the presence of the object or the size of the object. By the change in the vibration state of the vibration plate, the manner of change in the electrostatic capacitance (or impedance) of a virtual capacitor comprised of the first detection electrode and the second detection electrode changes. The determination unit determines the passage of the object and/or the size of the object on the basis of the change in the electrostatic capacitance. Accordingly, the determination unit can determine the passage of the object in the specific space and/or the size of the object on the basis of the change in the partial voltage of a virtual capacitor C4 in the circuit in which a capacitor C3 having the predetermined capacitance and the virtual capacitor C4 are serially connected, for example. Specifically, the sensor unit having the structure described above is configured to convert the vibration state of the vibration plate and its change into an electrical signal. Accordingly, the structure of the sensor unit described above is sometimes referred to as a structure of an "electrostatic microphone" (the configurations B02 to B13 described below describe the variations of the configuration B1 of the passage detection apparatus when the sensor unit has the structure of the "electrostatic microphone").

In the configuration described above, various materials can be selected as the vibration plate. For example, a film of synthetic resin can be used as the vibration plate. In this case, the first detection electrode can easily be made into a thin film. Thus, the overall rigidity of the vibration plate and the first detection electrode is reduced, so that the vibration plate greatly vibrates even by a very small vibration of the medium. Therefore, the slight change of the vibration state of the medium can appear as the great change of the vibration state of the vibration plate. Accordingly, the sensitivity of detecting the passage of the object by the passage detection apparatus is further enhanced.

B02

In the above-mentioned configuration B01, the vibration generating source may be comprised of a piezoelectric/electrostrictive element. Specifically, in this case, the vibration generating source is comprised of a first piezoelectric/electrostrictive element having a first dielectric layer, and a drive electrode and a first reference electrode that are formed at both sides of the first dielectric layer.

In this configuration, since a drive voltage is applied between the first reference electrode and the drive electrode, the vibration is generated from the first piezoelectric/electrostrictive element on the basis of the inverse piezoelectric effect. This vibration is propagated to the second piezoelectric/electrostrictive element through the medium. The determination unit determines whether the object passes in the specific space or not and/or determines the size of the object on the basis of the change of the vibration state of the vibration plate. According to this configuration, whether the object passes through the specific space or not and/or the size of the object can surely be determined with simplified structure, regardless of the conductivity of the object.

B03

In the above-mentioned configuration B02, the first substrate and the first piezoelectric/electrostrictive element may be integrally formed by sintering. Accordingly, the fixing force between the first substrate to the first piezoelectric/electrostrictive element is enhanced. Consequently, a passage detection apparatus having high durability can be obtained by a simple manufacturing process.

B04

In any one of the above-mentioned configurations B01 to B03, a first substrate made of a plate-like dielectric layer and supporting the vibration generating source (the first piezoelectric/electrostrictive element) may further be provided, and the specific space may be faulted from the space between an inner surface of the first substrate and an inner surface of the vibration plate. In this case, the specific space is formed from the space between the first substrate and the vibration plate. Ceramic or the like is preferably used for the dielectric layer composing the first substrate and the vibration plate, for example.

According to the configuration described above, the vibration generating source (the first piezoelectric/electrostrictive element) is surely be supported by the first substrate. Therefore, the vibration toward the medium from the vibration generating source can more efficiently be propagated. Moreover, the specific space that has the microstructure and through which the object passes can surely be formed to have a desired shape and size.

B05

In the above-mentioned configuration B04, the vibration generating source (the first piezoelectric/electrostrictive element) may be held on an outer surface, which is the surface reverse to the inner surface, of the first substrate.

In the configuration described above, the first substrate is arranged in such a manner that the inner surfaces of the first substrate and the vibration plate face the specific space (in such a manner that the vibration generating source is not exposed to the specific space). Thus, the passage of the object and/or the size of the object can satisfactorily be determined, even when the object is liquid or conductive. When the object is solid, the passage of the object can be detected with enhanced sensitivity. It is to be noted that the inner surfaces of the first substrate and the vibration plate may be exposed to the specific space, or a coating layer made of an insulating material may be formed on the inner surfaces.

B06

In any one of the above-mentioned configurations B04 and B05, the first substrate and the second substrate may be arranged such that the distance L in the widthwise direction of the specific space (the direction perpendicular to the moving direction of the object and the direction forming the shortest distance between the first substrate and the second substrate) satisfies the equation of $L=n\lambda$, or $L=(m/2)\cdot\lambda$, wherein the wavelength of the vibration propagating through the medium is defined as λ, and n and m are defined as a natural number. In particular, in the above-mentioned configuration B03, the first substrate and the vibration plate may be arranged in such a manner that the distance between the inner surface of the first substrate and the inner surface of the vibration plate becomes the distance L. Accordingly, the vibration can more efficiently be propagated.

B07

In any one of the above-mentioned configurations B04 to B06, the first substrate may include a plate-like thin part and a plate-like thick part that is formed at both sides of the thin part and is thicker than the thin part, wherein the vibration generating source may be attached to the thin part of the first substrate.

In the above-mentioned configuration, the first substrate is formed in such a manner that the thin part is bridged between the adjacent thick parts. Therefore, the thin part is efficiently vibrated by the vibration generating source (the first piezoelectric/electrostrictive element), whereby the vibration with high output can be propagated through the medium in the specific space.

It is to be noted that the thin part and thick part may be integrally formed from the same material. Alternatively, the thin part may be made of a material different from the material of the thick part. In this case, the thin part may be integrally formed with the thick part with a sintering or the like, or may be fixed to the thick part by bonding or welding.

B08

In the above-mentioned configuration B07, the first substrate may be formed such that an outer surface of the thin part and an outer surface of the thick part are continuous on a same plane, and the specific space may be formed to include a space enclosed by an inner surface of the thin part at the first substrate and a side face of the thick part at the first substrate.

In the configuration described above, a concave part composing the specific space is formed at the inner side (the side facing the specific space) of the first substrate. Therefore, a part of the specific space can be formed within the range of the thickness of the first substrate. Accordingly, the passage detection apparatus can be miniaturized.

B09

In the above-mentioned configuration B08, the side face of the thick part at the first substrate may be configured to be capable of reflecting sound wave or ultrasonic wave.

In the configuration described above, sound wave or ultrasonic wave can be reflected with high efficiency by the inner wall surface of the concave part forming the specific space. Therefore, directivity when the ultrasonic wave or the like propagates through the medium is enhanced. Accordingly, the passage of the object or the like can satisfactorily be detected even though output of the vibration generating source is reduced to decrease the power consumption.

B10

In any one of the above-mentioned configurations B01 to B09, the sensor unit may be configured such that thick plates which are plate-like members and are thicker than the vibration plate are arranged at both ends of the vibration plate forming the electrostatic microphone at the sensor unit, wherein the vibration plate is supported by the thick plates.

According to the configuration described above, the vibration plate is bridged between the adjacent thick plates. Therefore, the vibration plate can be vibrated with high efficiency by the vibration propagating through the medium. Accordingly, the passage of the object or the like can be detected with high sensitivity.

B11

In the above-mentioned configuration B10, the vibration plate and the thick plate may be integrally configured such that an outer surface of the vibration plate and an outer surface of the thick plate are continuous on a same plane, and the specific space may be configured to include a space enclosed by the inner surface of the vibration plate and a side face of the thick plate.

In the configuration described above, a concave part composing the specific space is formed at the inner side (the side facing the specific space) of the vibration plate. The concave part is formed within the range of the thickness of the thick plate. Therefore, a part of the specific space can be formed within the range of the thickness of the thick plate. Accordingly, the passage detection apparatus can be miniaturized. In particular, when the first substrate is configured in a similar fashion (refer to the configuration B07), nearly entire specific space can be formed within the range of the thickness obtained by superimposing the first substrate and the thick plate. Consequently, the passage detection apparatus can further be miniaturized.

B12

In the above-mentioned configuration B11, the side face of the thick plate may be formed to be smooth to an extent of being capable of nearly totally reflecting sound wave or ultrasonic wave.

In the configuration described above, sound wave or ultrasonic wave can be reflected with high efficiency by the inner wall surface of the specific space formed by the side face of the thick plate. Therefore, directivity when the ultrasonic wave or the like propagates through the medium is enhanced. Accordingly, the thin part can be vibrated with high efficiency by the vibration propagated through the medium. In particular, it is preferable that the first substrate has the same structure (refer to the configuration B08). Accordingly, the vibration in the specific space formed at the inner side of the portion where the member comprised of the vibration plate and the thick plate and the first substrates are superimposed can be propagated with high directivity.

B13

In any one of the above-mentioned configurations B01 to B12, the vibration generating source may be comprised of a piezoelectric/electrostrictive element having a multi-layer structure.

According to the configuration described above, the output of the vibration from the vibration generating source can be more increased. Therefore, the passage of the object and/or the size of the object can satisfactorily be detected.

Configuration C: Electrostatic Capacitive Sensor Type

In order to achieve the foregoing object, the passage detection apparatus according to the present invention includes the following configurations.

C01

The passage detection apparatus according to the present invention includes a plate-like first electrode, a plate-like second electrode arranged parallel to the first electrode across the specific space, and a determination unit that is configured to determine the passage of a micro object (hereinafter simply referred to as "the object") in the specific space on the basis of the electrostatic capacitance between the first electrode and the second electrode.

In the configuration described above, the electrostatic capacitance (or impedance) of a virtual capacitor comprised of the first electrode, the second electrode, and the medium (e.g., air) in the specific space changes according to the presence of the object. Therefore, the determination unit can determine whether the object passes through the specific space by acquiring the change in the partial voltage of the virtual capacitor C2 in the circuit in which a capacitor C1 having the predetermined capacitance and the virtual capacitor C2 are serially connected, for example.

The electrostatic capacitance of the virtual capacitor also changes according to the size of the object. Accordingly, the determination unit can determine the size of the object on the basis of the partial voltage of the virtual capacitor C2.

C02

In the above-mentioned configuration C01, a first electrode support layer that is made of a plate-like dielectric layer and supports the first electrode and a second electrode support layer that is made of a plate-like dielectric layer and supports the second electrode may further be provided. In this case, the specific space is made by a space between an inner surface, which is the surface at the side of the specific space, of the first electrode support layer and an inner surface, which is the surface at the side of the specific space, of the second electrode support layer. Ceramic is preferably used for the dielectric layer composing the first electrode support layer and the second electrode support layer, for example.

According to the configuration described above, the first electrode and the second electrode are surely supported by the first electrode support layer and the second electrode support layer. Therefore, the distance between the first electrode and the second electrode can surely be set to a desired distance. Accordingly, the specific space that has a microstructure and through which the object passes can surely be formed into a desired shape and size. Also, since the distance between the electrodes in the virtual capacitor is stably formed, whether the objects passes or not or the size of the object can more correctly be determined.

C03

In the above-mentioned configuration C02, the first electrode may be supported on the inner surface of the first electrode support layer and the second electrode may be supported on the inner surface of the second electrode support layer.

In the configuration described above, the first electrode is supported by the first electrode support layer so as to face the specific space, while the second electrode is supported by the second electrode support layer so as to face the specific space. The virtual capacitor is comprised of the first electrode, the second electrode, and the medium (e.g., air) in the specific space, so that the first electrode support layer and the second electrode support layer do not compose the virtual capacitor. Accordingly, the passage of the object and/or the size of the object can be determined with excellent sensitivity with a simplified structure.

C04

In the above-mentioned configuration C03, it is preferable that a coating layer made of an insulating material is formed on the inner surfaces of the first electrode support layer and the second electrode support layer so as to cover the first electrode and the second electrode. By virtue of this configuration, the passage of the object and/or the size of the object can be satisfactorily determined even when the object is liquid or conductive.

C05

In the above-mentioned configuration C02, the first electrode may be formed on an outer surface, which is reverse to the inner surface, of the first electrode support layer, and the second electrode may be formed on an outer surface, which is reverse to the inner surface, of the second electrode support layer.

In the configuration described above, the first electrode support layer and the second electrode support layer are arranged in such a manner that the inner surfaces of the first electrode support layer and the second electrode support layer face the specific space (in such a manner that the first electrode and the second electrode are not exposed to the specific space). Thus, the passage of the object and/or the size of the object can satisfactorily be determined, even when the object is liquid or conductive. It is to be noted that the inner surfaces of the first electrode support layer and the second electrode support layer may be exposed to the specific space, or a coating layer made of an insulating material may be formed on the inner surfaces.

Configuration D: Sound Wave+Electrostatic Capacitive Sensor Type

In order to achieve the foregoing object, the passage detection apparatus according to the present invention includes the following configurations.

D01

The passage detection apparatus according to the present invention includes a vibration generating source, a vibration sensor unit, a first electrode, a second electrode, and a determination unit. The vibration sensor unit is arranged at the position corresponding to the vibration generating source across the specific space, and is configured to be capable of generating an output according to the vibration propagating via a medium in the specific space. The second electrode is arranged parallel to the plate-like first electrode across the specific space. The determination unit is configured to determine the passage of the object in the specific space on the basis of the output at the vibration sensor unit, and the electrostatic capacitance between the first electrode and the second electrode.

In the configuration described above, the propagation state of the vibration of the medium in the specific space changes depending upon the presence of the object. Accordingly, the determination unit can determine whether the object passes or not in the specific space on the basis of the change in the output (e.g., output voltage) by the vibration sensor unit, for example. The propagation state of the vibration at the medium (e.g., air) in the specific space also changes according to the size of the object. Therefore, the determination unit can also determine the size of the object.

The electrostatic capacitance (or impedance) of a virtual capacitor comprised of the first electrode, the second electrode, and the medium (e.g., air) in the specific space changes according to the presence of the object. Therefore, the determination unit can determine whether the object passes through the specific space by acquiring the change in the partial voltage of the virtual capacitor C2 in the circuit in which the capacitor C1 having the predetermined capacitance and the virtual capacitor C2 are serially connected, for example. The electrostatic capacitance of the virtual capacitor also changes according to the size of the object. Accordingly, the determination unit can determine the size of the object on the basis of the partial voltage of the virtual capacitor C2.

As described above, the passage detection apparatus according to the present invention employs the configuration in which a structure of a so-called electrostatic capacitive sensor type (refer to the configurations C01~C05) and a structure of a so-called sonic (ultrasonic) sensor (refer to the configurations A01~A16, B01~B13) are combined.

In the configuration described above, the electrical signal outputted from the first electrode and the second electrode in the electrostatic capacitive sensor structure is based upon dielectric constant of the object passing through the specific space. On the other hand, the electrical signal outputted from the vibration sensor unit in the sonic (ultrasonic) sensor is based upon the rheology characteristic of the object passing through the specific space, such as density, etc. The output from the structure of the electrostatic capacitive sensor and the output from the structure of the sonic (ultrasonic) sensor are based upon the different characteristic of the object passing through the specific space.

Therefore, in this configuration, the determination unit can determine whether the object passes through the specific space or not and/or the size of the object on the basis of the detection value in the structure of the electrostatic capacitive sensor and the detection value in the structure of the sonic (ultrasonic) sensor. Specifically, for example, the determination unit can determine the passage of the object and/or the size of the object by performing an appropriate statistic process such as averaging on the basis of one detection value and the other detection value. Alternatively, the determination unit can determine the passage of the object and/or the size of the object by appropriately selecting one of the detection values according to the situation.

The determination unit alternatively can determine the passage of the object and/or the size of the object on the basis of the waveform of the electric signal obtained by performing an appropriate process on the electric circuit (superimposition, filtering, etc.) to the electric signal outputted from the vibration sensor in the structure of the sonic (ultrasonic) sensor and the electric signal outputted from the first and second electrodes in the structure of the electrostatic capacitive sensor.

The processing method of the electric signals outputted from the vibration sensor in the structure of the sonic (ultrasonic) sensor and the first and second electrodes in the structure of the electrostatic capacitive sensor is not particularly limited in the present configuration.

According to the present configuration, the passage of the object and/or the size of the object can be detected with enhanced reliability by using the electric signal outputted from the vibration sensor in the structure of the sonic (ultrasonic) sensor and the electric signal outputted from the first and second electrodes in the structure of the electrostatic capacitive sensor, regardless of the property (size or chargeability) of the object.

In the passage detection apparatus according to the present invention, various structures that can be employed in the structure of the electrostatic capacitive sensor (refer to the configurations C02~C05) and the various structures (refer to the configurations A02~B12) that can be employed in the structure of the sonic (ultrasonic) sensor can be employed as combined within the scope of consistency.

D02

In the above-mentioned configuration D01, a first substrate made of a plate-like dielectric layer and supporting the vibration generating source and the first electrode and a second substrate made of a plate-like dielectric layer and supporting the vibration sensor unit and the second electrode may be further provided. In this case, the specific space is formed from a space between an inner surface of the first substrate and an inner surface of the second substrate. Ceramic or the like is preferably used, for example, as the dielectric layer composing the first substrate and the second substrate.

According to the configuration described above, the specific space that has a microstructure and through which the object passes can surely be formed into a desired shape and size.

In the configuration described above, the vibration generating source and the first electrode are surely supported by the first substrate, and the vibration sensor and the second electrode are surely supported by the second substrate. Therefore, the vibration toward the medium from the vibration generating source can more efficiently be propagated. Further, the vibration from the medium can more efficiently be received by the vibration sensor. Moreover, since the distance between the first electrode and the second electrode is set to a desired distance, and the distance between the electrodes in the virtual capacitor is stably formed, whether the objects passes or not or the size of the object can more correctly be determined.

D03

The passage detection apparatus having the configuration D02 may be configured as follows. The vibration generating source is comprised of a first piezoelectric/electrostrictive element having a first dielectric layer, and a drive electrode and a first reference electrode that are formed at both sides of the first dielectric layer. The vibration sensor unit is comprised of a second piezoelectric/electrostrictive element having a second dielectric layer, and a signal output electrode and a second reference electrode that are fowled at both sides of the second dielectric layer.

The first electrode composing the electrostatic capacitive sensor is comprised of the drive electrode or the first reference electrode in the first piezoelectric/electrostrictive element, whichever is closer to the second piezoelectric/electrostrictive element. Further, the second electrode composing the electrostatic capacitive sensor is comprised of the signal output electrode or the second reference electrode in the second piezoelectric/electrostrictive element, whichever is closer to the first piezoelectric/electrostrictive element.

According to this configuration, the passage detection apparatus according to the present invention having the structure in which the structure of the electrostatic capacitive sensor and the structure of the sonic (ultrasonic) sensor are combined can be provided with a simplified structure.

D04

In the above-mentioned configuration D03, the first piezoelectric/electrostrictive element and the first electrode may be supported on an inner surface of the first substrate that is the surface at the side of the specific space, and the second piezoelectric/electrostrictive element and the second electrode may be supported on an inner surface of the second substrate that is the surface at the side of the specific space.

In the configuration described above, the first piezoelectric/electrostrictive element and the second piezoelectric/electrostrictive element are arranged so as to face the specific space. Further, the first electrode and the second electrode are arranged so as to face the specific space. The space between the first electrode and the second electrode forms the specific space, and the vibration is propagated from the first piezoelectric/electrostrictive element to the second piezoelectric/electrostrictive element through the medium in the specific space. The change in the electrostatic capacitance in the space between the first electrode and the second electrode is also detected. Therefore, the passage of the object and/or the size of the object can be determined with enhanced sensitivity by a simplified structure.

D05

In the above-mentioned configuration D04, a coating layer made of an insulating material may be formed so as to cover the first piezoelectric/electrostrictive element, the second piezoelectric/electrostrictive element, the first electrode, and the second electrode.

According to this configuration, a stable performance can be obtained, even if the passage detection apparatus is used under high-humid environment.

The object is prevented from being directly deposited onto the first piezoelectric/electrostrictive element, the second piezoelectric/electrostrictive element, the first electrode, and the second electrode, when the object is liquid or conductive. Accordingly, the occurrence of short-circuit between the electrodes having a different potential can be prevented. Accordingly, the passage of the object and/or the size of the object can satisfactorily be determined, even when the object is liquid or conductive.

D06

In the above-mentioned configuration D03, the first piezoelectric/electrostrictive element and the first electrode may be held on an outer surface, which is reverse to an inner surface at the side of the specific space, of the first substrate, and the second piezoelectric/electrostrictive element and the second electrode may be held on an outer surface, which is reverse to an inner surface at the side of the specific space, of the second substrate.

In the configuration described above, the first substrate and the second substrate are arranged in such a manner that the inner surfaces of the first substrate and the second substrate face the specific space (in such a manner that the first piezoelectric/electrostrictive element, the second piezoelectric/electrostrictive element, the first electrode, and the second electrode are not exposed to the specific space). Thus, the passage of the object and/or the size of the object can satisfactorily be determined, even when the object is liquid or conductive. It is to be noted that the inner surfaces of the first substrate and the second substrate may be exposed to the specific space, or a coating layer made of an insulating material may be formed on the inner surfaces.

D07

In any one of the above-mentioned configurations D03 to D06, the first substrate and the second substrate may be arranged such that the distance L in the widthwise direction of the specific space (the direction perpendicular to the moving direction of the object and the direction forming the shortest distance between the first substrate and the second substrate) satisfies the equation of $L=n\lambda$ or $L=(m/2)\cdot\lambda$, wherein the wavelength of the vibration propagating through the medium is defined as $\lambda$, and n and m are defined as a natural number. In particular, in the above-mentioned configuration D07, the first substrate and the second substrate may be arranged in such a manner that the distance between the inner surface of the first substrate and the inner surface of the second substrate becomes the distance L. Accordingly, the vibration from the first piezoelectric/electrostrictive element to the second piezoelectric/electrostrictive element can more efficiently be propagated.

D08

In any one of the configurations D03 to D7, the first substrate, the first piezoelectric/electrostrictive element, and the first electrode may be integrally formed by sintering, and the second substrate, the second piezoelectric/electrostrictive element, and the second electrode may be integrally formed by sintering. Accordingly, the fixing force between each substrate to the corresponding piezoelectric/electrostrictive element and the corresponding electrode is enhanced. Consequently, a passage detection apparatus having high durability can be obtained by a simple manufacturing process.

D09

In any one of the above-mentioned configurations D03 to D08, the first substrate may include a plate-like thin part and a plate-like thick part that is formed at both sides of the thin part and is thicker than the thin part, wherein the vibration generating source and the first electrode may be attached to the thin part of the first substrate.

In the above-mentioned configuration, the first substrate is formed in such a manner that the thin part is bridged between the adjacent thick parts. Therefore, the vibration can be generated from the first piezoelectric/electrostrictive element, serving as the vibration generating source, with high output.

D10

In the above-mentioned configuration D09, the first substrate may be formed such that an outer surface of the thin part and an outer surface of the thick part are continuous on a same plane, and the specific space may be fowled to include a space enclosed by an inner surface of the thin part at the first substrate and a side face of the thick part at the first substrate.

In the configuration described above, a concave part composing the specific space is formed at the inner side (the side facing the specific space) of the first substrate, and the thin part is formed so as to be bridged between the adjacent thick parts at the outer side of the first substrate. Therefore, a part of the specific space can be formed within the range of the thickness of the first substrate. Accordingly, the passage detection apparatus can be miniaturized.

D11

In the above-mentioned configuration D10, the side face of the thick part at the first substrate may be configured to be capable of reflecting sound wave or ultrasonic wave.

In the configuration described above, sound wave or ultrasonic wave can be reflected with high efficiency by the inner wall surface of the concave part forming the specific space. Therefore, directivity when the ultrasonic wave or the like propagates through the medium is enhanced. Accordingly, the passage of the object and/or the size of the object can satisfactorily be detected even though the input voltage of the first piezoelectric/electrostrictive element, which constitutes the vibration generating source, is reduced to decrease the power consumption.

D12

In any one of the above-mentioned configurations D03 to D11, the second substrate may include a thin part and a thick part, and the sensor unit and the second electrode may be attached to the thin part of the second substrate. The thin part is formed into a flat plate shape. The thick part is a member having a flat plate shape thicker than the thin part. The thick part is formed at both sides of the thin part.

According to the configuration described above, the second substrate is formed in such a manner that the thin part is bridged between the adjacent thick parts. Therefore, the thin part can be vibrated with high efficiency by the vibration propagating through the medium. Accordingly, the passage of the object and/or the size of the object can be detected with high sensitivity.

D13

In the above-mentioned configuration D12, the second substrate may be formed such that an outer surface of the thin part and an outer surface of the thick part are continuous on a same plane, and the specific space may be configured to include a space enclosed by an inner surface of the thin part at the second substrate and a side face of the thick part at the second substrate.

In the configuration described above, a concave part composing the specific space is formed at the inner side (the side facing the specific space) of the second substrate, and the thin part is formed so as to be bridged between the adjacent thick parts at the outer side of the second substrate. Therefore, a part of the specific space can be formed within the range of the thickness of the second substrate. Accordingly, the passage detection apparatus can be miniaturized. In particular, nearly entire specific space can be formed within the range of the thickness, obtained by superimposing the first substrate and the second substrate, by forming the first substrate in the same manner as the second substrate (refer to the configuration D11). Consequently, the passage detection apparatus can further be miniaturized.

D14

In the above-mentioned configuration D13, the side face of the thick part at the second substrate may be formed to be smooth to an extent of being capable of nearly totally reflecting sound wave or ultrasonic wave.

In the configuration described above, sound wave or ultrasonic wave can be reflected with high efficiency by the inner wall surface of the concave part composing the specific space. Therefore, directivity when the ultrasonic wave or the like propagates through the medium is enhanced. Accordingly, the thin part can be vibrated with high efficiency by the vibration propagating through the medium. In particular, it is preferable that the first substrate is formed in the same manner as the second substrate (refer to the configuration D12). Accordingly, the vibration from the first piezoelectric/electrostrictive element to the second piezoelectric/electrostrictive element in the specific space formed at the inner side of the portion where the first and the second substrates are superimposed can be propagated with high directivity.

D15

In any one of the above-mentioned configurations D01 to D14, the vibration generating source may be comprised of a piezoelectric/electrostrictive element having a multi-layer structure.

Configuration E: Sonic+Electrostatic Capacitive Sensor Type/Electrostatic Microphone-Type Vibration Sensor Unit The passage detection apparatus having the configuration D02 may be configured as follows.

E01

The second substrate includes a vibration part having a thin plate-like shape and supported so as to be vibrated by the vibration propagating through the medium in the specific space from the vibration generating source. The vibration sensor unit includes a first detection electrode, a support plate, and a second detection electrode. The first detection electrode is provided at the vibration part. The support plate is arranged parallel to the second substrate so as to face the vibration part with a predetermined gap at the outside of the specific space. The second detection electrode is formed on the surface, facing the vibration plate, of the support plate, and is arranged parallel to the first detection electrode. The first detection electrode is comprised of the second electrode, and the determination unit is configured to determine the passage of the object in the specific space on the basis of the electrostatic capacitance between the first detection electrode and the second detection electrode. Specifically, in this configuration, the vibration sensor unit has the structure of the electrostatic microphone.

In the configuration described above, the propagation state of the vibration of the medium in the specific space toward the vibration plate changes according to the presence of the object or the size of the object. Therefore, the vibration state of the vibration plate changes according to the presence of the object or the size of the object. By the change in the vibration state of the vibration plate, the manner of changing the electrostatic capacitance (or impedance) of the electrostatic capacitance of the second virtual capacitor comprised of the first detection electrode and the second detection electrode changes. The determination unit determines the passage of the object and/or the size of the object by also referring to the change in the electrostatic capacitance of the second virtual capacitor.

Specifically, for example, the determination unit can determine the passage of the object in the specific space and/or the size of the object on the basis of two outputs described below: (1) The change in the partial voltage of the virtual capacitor C2 in the circuit in which a capacitor C1 having the predetermined capacitance and the virtual capacitor C2 are connected in series. (2) The change in the partial voltage of the virtual capacitor C4 in the circuit in which a capacitor C3 having the predetermined capacitance and the virtual capacitor C4 are connected in series.

E02

In the above-mentioned configuration E01, the first electrode may be supported on an inner surface of the first substrate that is the surface at the side of the specific space, and the second electrode may be supported on an inner surface of the second electrode that is the surface at the side of the specific space.

In the above-mentioned configuration, the first electrode is supported by the first substrate so as to face the specific space. Further, the second electrode is supported by the second substrate so as to face the specific space. The virtual capacitor C2 is comprised of the first electrode, the second electrode, and the medium (air) in the specific space, wherein the first substrate and the second substrate do not compose the virtual capacitor C2. Therefore, the passage of the object and/or the size of the object can be determined with excellent sensitivity by the simplified structure.

E03

In the above-mentioned configuration E02, a coating layer made of an insulating material is formed so as to cover the first electrode and the second electrode. By virtue of this configuration, the passage of the object and/or the size of the object are satisfactorily determined even when the object is liquid or conductive.

E04

In the above-mentioned configuration E01, the first electrode may be formed on an outer surface, which is reverse to an inner surface at the side of the specific space, of the first substrate, and the second electrode may be formed on an outer surface, which is reverse to an inner surface at the side of the specific space, of the second substrate.

In the configuration described above, the first substrate and the second substrate are arranged in such a manner that the inner surfaces of the first substrate and the second substrate face the specific space (in such a manner that the first electrode and the second electrode are not exposed to the specific space). Thus, the passage of the object and/or the size of the object can satisfactorily be determined, even when the object is liquid or conductive. It is to be noted that the inner surfaces of the first substrate and the second substrate may be exposed to the specific space, or a coating layer made of an insulating material may be formed on the inner surfaces.

E05

In the above-mentioned configuration E05, the first substrate and the second substrate may be arranged such that the distance L between the inner surface of the first substrate and the inner surface of the second substrate satisfies the equation of $L=n\lambda$ or $L=(m/2)\cdot\lambda$, wherein the wavelength of the vibration propagating through the medium is defined as $\lambda$, and n and m are defined as a natural number. Accordingly, the vibration can more efficiently be propagated, so that the passage of the object and/or the size of the object can be detected with enhanced sensitivity.

E06

The passage detection apparatus having any one of the above-mentioned configurations E01 to E05 may be configured as follows. The vibration generating source is comprised of a first piezoelectric/electrostrictive element having a first dielectric layer, a drive electrode and a first reference electrode. The drive electrode and the first reference electrode are formed at both sides of the first dielectric layer. The first electrode is comprised of the first reference electrode or the drive electrode.

According to this configuration, the passage detection apparatus according to the present invention having the structure in which the structure of the electrostatic capacitive sensor and the structure of the sonic (ultrasonic) sensor are combined can be provided with a simplified structure.

E07

In the above-mentioned configuration E06, the first substrate, the first piezoelectric/electrostrictive element, and the first electrode may be integrally formed by sintering. Accordingly, the fixing force between the first substrate and the first electrode as well as the first piezoelectric/electrostrictive element is enhanced. Consequently, a passage detection apparatus having high durability can be obtained by a simple manufacturing process.

E08

In any one of the above-mentioned configurations E01 to E07, the first substrate may include a thin part and a thick part, and the vibration generating source and the first electrode may be attached to the thin part of the first substrate. The thin part is formed into a flat plate shape. The thick part is a member having a flat plate shape thicker than the thin part. The thick part is formed at both sides of the thin part.

E09

In the above-mentioned configuration E08, the first substrate may be formed such that an outer surface of the thin part and an outer surface of the thick part are continuous on a same plane, and the specific space may be configured to include a space enclosed by an inner surface of the thin part at the first substrate and a side face of the thick part at the first substrate.

E10

In the above-mentioned configuration E09, the side face of the thick part at the first substrate may be formed so as to be capable of reflecting sound wave or ultrasonic wave.

E11

In any one of the above-mentioned configurations E01 to E10, the second substrate may have a plate-like thick part that is thicker than the vibration part. The thick part is formed at both sides of the vibration part. According to the configuration described above, the vibration part is arranged so as to be bridged between the thick parts, whereby the vibration part is efficiently vibrated.

E12

In the above-mentioned configuration E11, the second substrate may be formed such that an outer surface of the vibration part and an outer surface of the thick part are continuous on a same plane, and the specific space may be configured to include a space enclosed by an inner surface of the vibration part at the second substrate and a side face of the thick part at the second substrate.

E13

In the above-mentioned configuration E12, the side face of the thick part at the second substrate may be formed to be smooth to an extent of being capable of nearly totally reflecting sound wave or ultrasonic wave.

E14

In any one of the above-mentioned configurations E01 to E13, the vibration generating source may be comprised of a piezoelectric/electrostrictive element having a multi-layer structure.

F01

In the configurations A01 to A16, B01 to B13, D01 to D16, and E01 to E14, it is preferable that the resonance frequency of the vibration generating source is set so as to be generally equal to the resonance frequency of the sensor unit. By virtue of this configuration, the passage of the object and/or the size of the object can be detected with enhanced sensitivity at the sensor unit having the structure of the sonic (ultrasonic) sensor.

F02

In the above-mentioned configuration F01, drive means for driving the vibration generating source may be further provided, wherein the drive means may be configured to drive the vibration generating source by outputting, to the vibration generating source, a pulse signal having a cycle corresponding to the resonance frequency of the vibration generating source. With this configuration, the vibration can be generated with high efficiency at the vibration generating source having the structure of the sonic (ultrasonic) sensor.

F03

In the above-mentioned configuration F02, the drive means may be configured to output the pulse signal in synchronism with the passage timing of the object. With this configuration, the passage of the object and/or the size of the object can surely be detected.

F04

In any one of the above-mentioned configurations F01 to F03, the sensor unit may be configured to output a voltage according to the propagation state of the vibration from the vibration generating source, and the determination unit may be configured to detect the passage of the object in the specific space on the basis of the change in the output voltage of the sensor unit. With this configuration, the passage of the object and/or the size of the object can be detected with enhanced sensitivity at the sensor unit having the structure of the sonic (ultrasonic) sensor.

G01

In each of the above-mentioned configurations, an aperture plate that is a plate-like member having formed thereto an aperture, which is a through-hole through which the object can pass, may be further provided. The aperture plate is arranged at the end portion of the specific space at the inlet side of the object so as to cross the passage direction of the object. The aperture is formed to be smaller than the size of the specific space in the section perpendicular to the passage direction of the object.

According to the configuration described above, the flight state (e.g., advancing direction or rectilinearity) in the specific space can be detected with simplified structure by appropriately setting the positional relationship between the opening at the end portion of the specific space at the side of the inlet of the object and the aperture.

G02

The passage detection apparatus having any one of the above-mentioned configurations may have a shield member. The shield member includes an element noise reducing shield member and/or a circuit noise reducing shield member.

The element noise reducing shield member is provided such that the element portions for the transmission and reception are made opposite to each other and the portions other than the element portions are covered in all directions in the sensor unit and/or the vibration generating source. The circuit noise reducing shield member is configured such that the determination unit is covered, whereby the electrical noise applied to the determination unit is eliminated.

In the configuration described above, the electrical noise is eliminated by the shield member. Thus, the S/N ratio in the passage detection of the object is enhanced. Accordingly, more micro object can be detected with high precision.

G03

The passage detection apparatus having any one of the above-mentioned configurations may have a band pass filter. The band pass filter can be interposed between the sensor unit and the determination unit. Alternatively, the band pass filter can be provided at the determination unit. The band pass filter is configured to limit the frequency of the output from the sensor unit to the band around the desired resonance frequency (specifically, within the range of ±10% of the desired resonance frequency, for example).

In the configuration described above, a mechanical noise is eliminated that is based upon ambient sound wave or the vibration or the like of an unnecessary mode other than the vibration of the desired mode corresponding to the desired resonant frequency. Accordingly, the S/N ratio for the detection of the passage of the object is enhanced. Consequently, an object having more micro size can be detected with high precision.

G04

In each of the above-mentioned configurations, the vibration generating source and the sensor unit may be configured such that the resonance frequency of the vibration generating source and the resonance frequency of the sensor unit are generally equal to each other in a first vibration mode, and the resonance frequency of the vibration generating source and the resonance frequency of the sensor unit are different from each other in a second vibration mode that is different from the first vibration mode. Specifically, the vibration generating source may have the structure different from that of the sensor unit.

In the configuration described above, the output from the sensor unit based upon the vibration of the sensor unit other than the first vibration mode in the vibration generating source can be suppressed. Accordingly, the S/N ratio for the detection of the passage of the object is enhanced. Consequently, an object having more micro size can be detected with high precision.

BRIEF DESCRIPTION OF THE DRAWINGS

Various other objects, features and many of the attendant advantages of the present invention will be readily appreciated as the same becomes better understood by reference to the following detailed description of the preferred embodiment when considered in connection with the accompanying drawings, in which:

FIG. 11 is a block diagram schematically showing an electric circuit configuration applied to the passage detection apparatus according to the embodiment shown in FIGS. 10A and 10B;

FIG. 19 is an enlarged sectional view showing an example of the structure of the passage detection apparatus using the detection unit, serving as the vibration transmitting source, shown in FIG. 18;

DETAILED DESCRIPTION OF THE INVENTION

Now, a preferred embodiment (embodiment that the applicant of the present application considers as the best mode upon filing the present application) of the present invention will be described in detail with reference to the accompanying drawings.

<Construction of DNA Chip>

Figure 1:
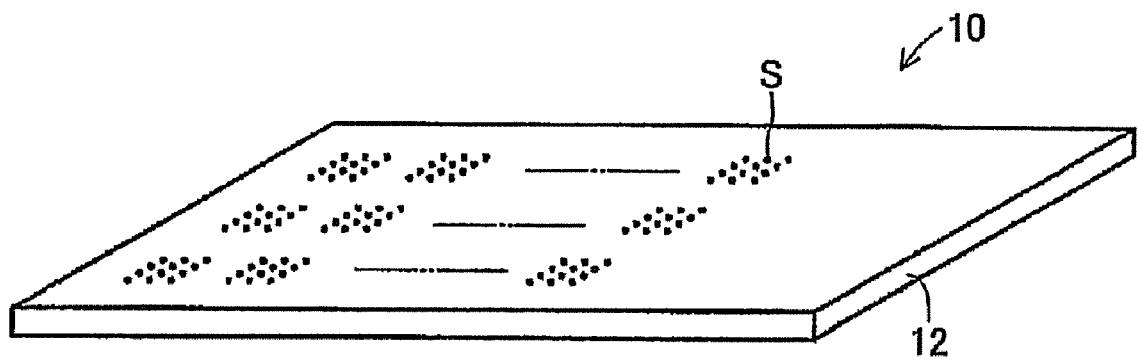
FIG. 1 is an external view (perspective view) illustrating the general structure of a DNA chip.
Figure 2:
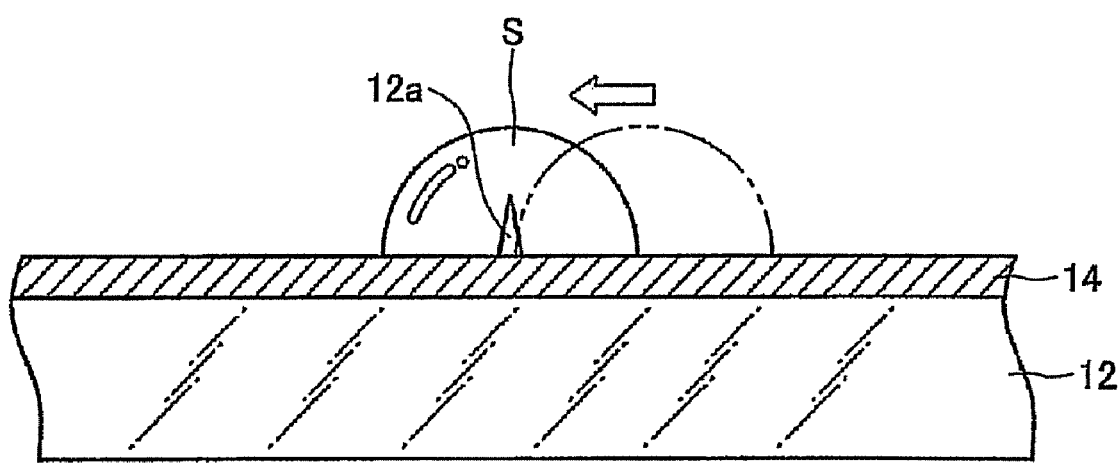
FIG. 2 is an enlarged sectional view of the DNA chip shown in FIG. 1.

FIG. 1 is an external view (a perspective view) illustrating the general structure of a DNA chip 10, and FIG. 2 is an enlarged sectional view of the DNA chip shown in FIG. 1.

As shown in FIG. 1, the DNA chip 10 is constructed by arranging plural micro spots S, which are formed by micro drops of a sample solution, on a DNA chip substrate 12, which is made of microscope slide glass.

As shown in FIG. 2, a protrusion 12a is formed on the DNA chip substrate 12 at a predetermined position where the corresponding micro spot S is to be formed. When the corresponding micro spot S drops while deviating from the predetermined position, the protrusion 12a serves to compensate for the positional deviation. Specifically, when a portion of the micro spot S is caught by the protrusion 12a (see a two-dot chain line), as shown in FIG. 2, the micro spot S is moved to the predetermined position by the surface tension of the micro spot S.

Also, a sample support layer 14, which is a poly-L-lysine layer having a hydrophilic property, is formed on the surface of the DNA chip substrate 12.

<Structure of Micropipette>

Figure 3:
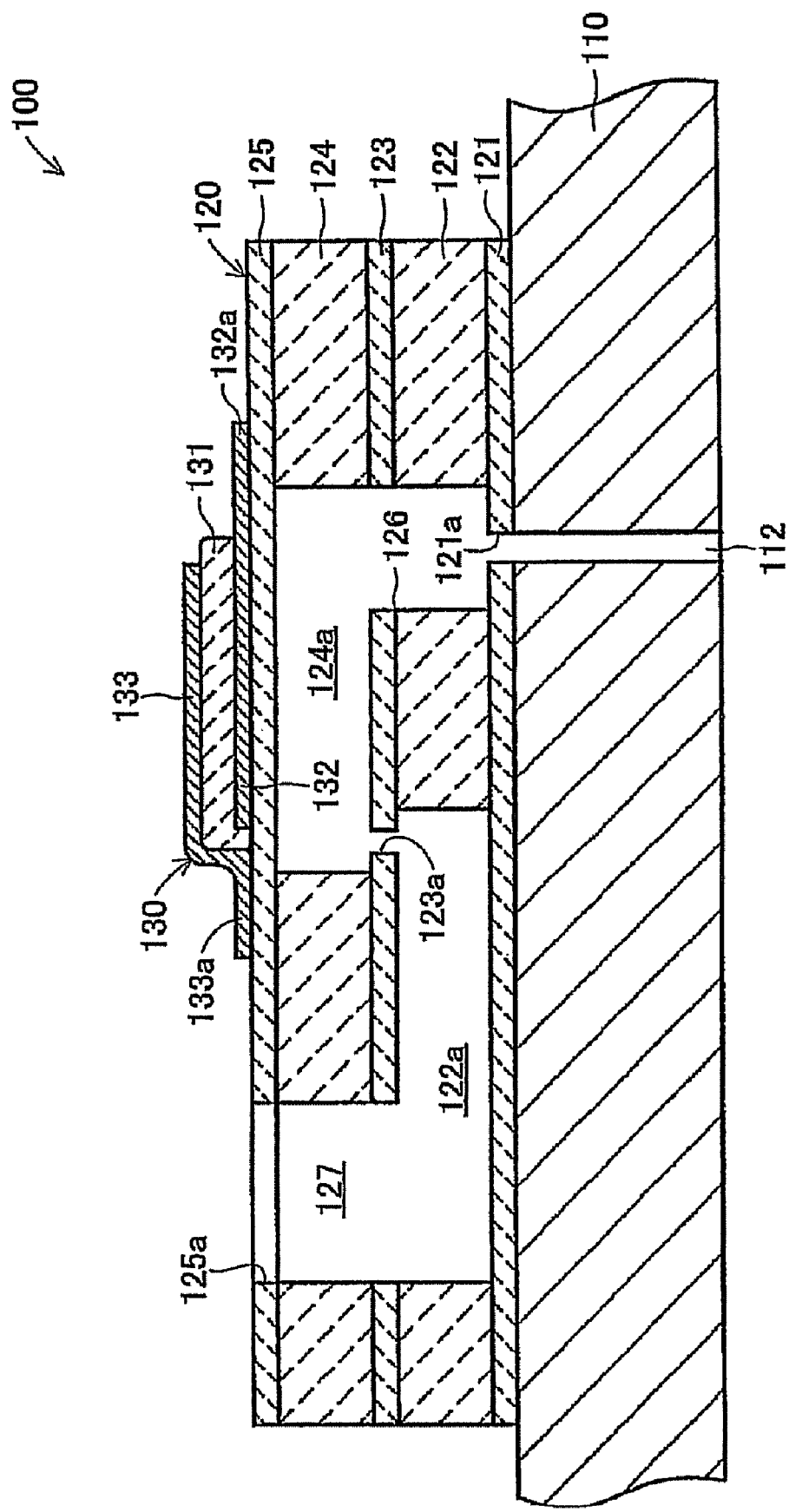
FIG. 3 is an enlarged sectional view of a micropipette.
Figure 4:
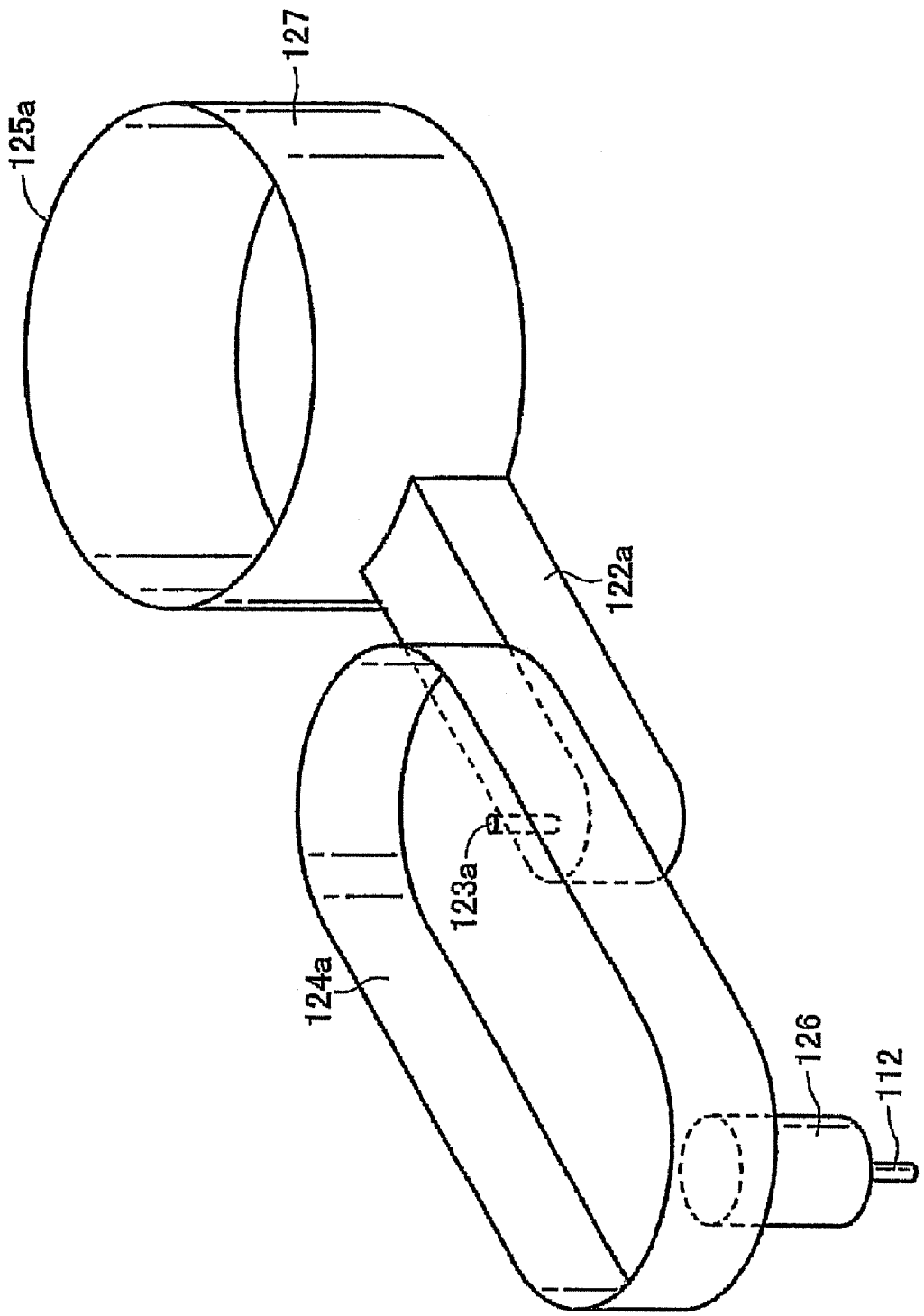
FIG. 4 is an enlarged and see-through perspective view illustrating the structure of a sample solution flow channel in the micropipette shown in FIG. 3.
Figure 5:
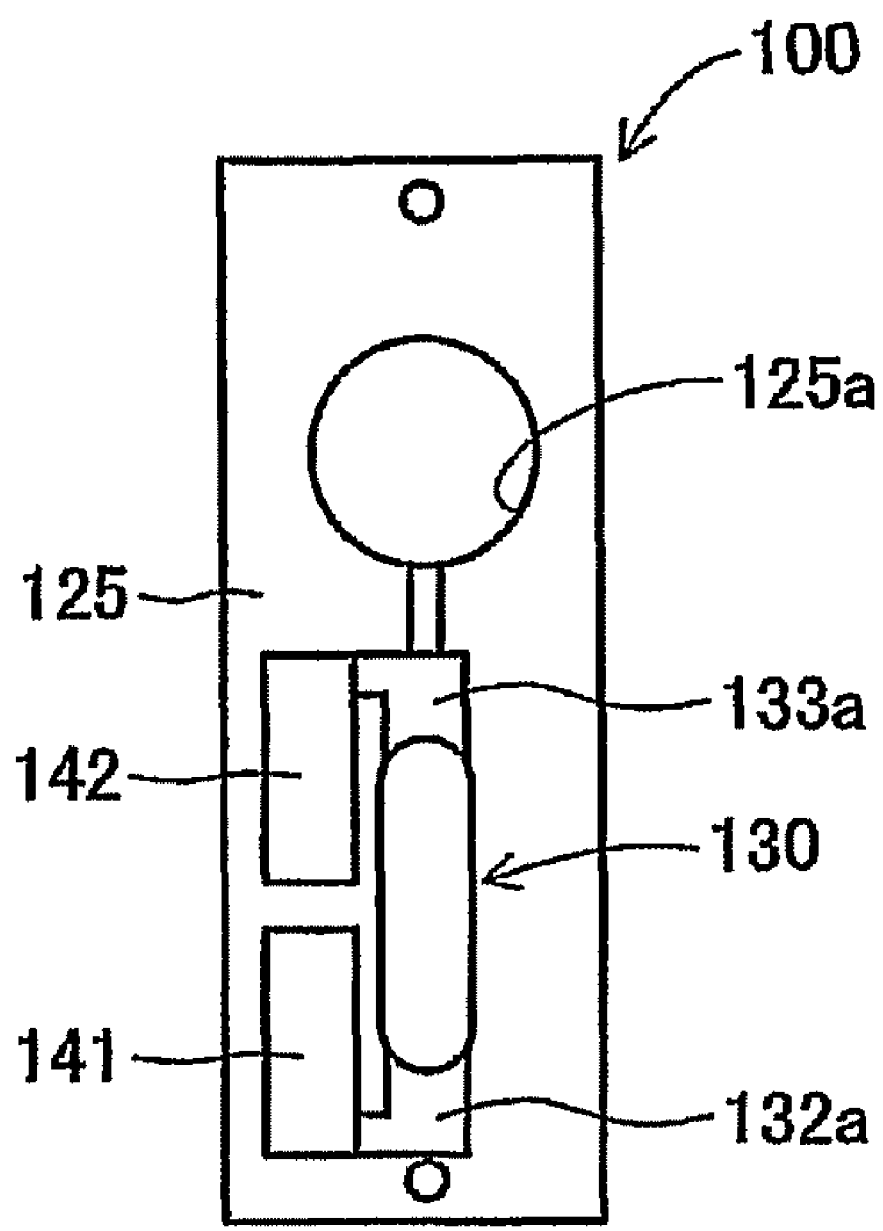
FIG. 5 is an enlarged plan view of the micropipette shown in FIG. 3.

Hereinafter, the structure of a micropipette, which is used to manufacture the above-described DNA chip 10, will be described in detail. FIG. 3 is an enlarged sectional view of the micropipette 100, FIG. 4 is a see-through perspective view illustrating the construction of a flow channel for a sample solution in the micropipette 100, and FIG. 5 is a plan view of the micropipette 100.

Referring to FIG. 3, the micropipette 100 includes a nozzle plate 110, a cavity unit 120 fixed to the upper surface of the nozzle plate 110, and an actuator unit 130 fixed to the upper surface of the cavity unit 120. In the nozzle plate 110 is formed a through-hole, i.e., a nozzle 112, through which the sample solution passes.

The nozzle plate 110 is formed from a thin ceramic plate. The material of the nozzle plate 110 includes, for example, zirconium oxide, aluminum oxide, magnesium oxide, aluminum nitride, and silicon nitride. Most preferably, a material mainly containing fully stabilized zirconium oxide or a material mainly containing partially stabilized zirconium oxide is used in terms of mechanical strength and a reaction to the material of a piezoelectric/electrostrictive film or an electrode film.

The cavity unit 120 includes a connection plate 121, a flow channel plate 122, an orifice plate 123, a cavity plate 124, and an injection port plate 125. The connection plate 121, the flow channel plate 122, the orifice plate 123, the cavity plate 124, and the injection port plate 125 are formed from a thin ceramic plate. The connection plate 121, the flow channel plate 122, the orifice plate 123, the cavity plate 124, the injection port plate 125, and the nozzle plate 110 are sintered while they are stacked in order on the nozzle plate 110. As a result, they are integrally formed at the nozzle plate 110.

The connection plate 121 is disposed at the connection between the cavity plate 120 and the nozzle plate 110 such that the connection plate 121 is joined to the upper surface of the nozzle plate 110. In the connection plate 121 is formed a through-hole having the same diameter as the nozzle 112, i.e., a nozzle communication hole 121a. The nozzle communication hole 121a is connected to a cavity 124a formed in the cavity plate 124 via a sample outlet hole 126. The sample outlet hole 126 is a through-hole having a diameter greater than that of the nozzle communication hole 121a. The sample outlet hole 126 is formed through the flow channel plate 122 and the orifice plate 123.

In the flow channel plate 122 is formed a sample supply channel 122a, through which the sample solution is supplied to the cavity 124a. The sample supply channel 122a and the cavity 124a are connected with each other via an orifice 123a, which is a through-hole, having a small diameter, formed in the orifice plate 123.

The injection port plate 125 is disposed at the uppermost layer of the cavity unit 120. In the injection port plate 125 is formed a sample injection port 125a, which is a through-hole for allowing the sample solution to be injected toward the sample supply channel 122a formed in the flow channel plate 122. The sample injection port 125a and the sample supply channel 122a formed in the flow channel plate 122 are connected with each other via a sample introduction hole 127, which is a through-hole. The sample introduction hole 127 is formed through the orifice plate 123 and the cavity plate 124.

As shown in FIG. 4, a sample solution flow channel is formed in the cavity unit 120 with the above-stated construction such that the sample solution flow channel extends from the sample injection port 125a to the nozzle 112. Specifically, the dimension of the orifice 123a is set such that, when the cavity 124a is pressurized, the sample solution in the cavity 124a does not flow backward to the sample supply channel 122a through the small-diameter orifice 123a but flows out toward the nozzle 112 through the sample outlet hole 126, and therefore, micro drops of the sample solution are ejected to the outside from the nozzle 112.

Referring back to FIG. 3, the actuator unit 130 includes a piezoelectric/electrostrictive layer 131, a lower electrode 132 fixed to the lower surface of the piezoelectric/electrostrictive layer 131, and an upper electrode 133 fixed to the upper surface of the piezoelectric/electrostrictive layer 131. The piezoelectric/electrostrictive layer 131 is disposed at a predetermined position corresponding to the cavity 124a (i.e., right above the cavity 124a). The lower electrode 132 is fixed to the upper surface of the injection port plate 125, and therefore, the actuator unit 130 is fixed to the upper surface of the cavity unit 120. The actuator unit 130 is constructed such that the actuator unit 130 changes the interior volume of the cavity 124a, when drive voltage is applied between the lower electrode 132 and the upper electrode 133, to eject a predetermined amount of the sample solution from the nozzle 112.

The lower electrode 132 is connected to a lower electrode wiring pattern 132a, which is a conductive film formed at the upper surface of the injection port plate 125. The upper electrode 133 is connected to an upper electrode wiring pattern 133a, which is a conductive film formed at the upper surface of the injection port plate 125.

As shown in FIG. 5, a lower electrode input terminal 141 is formed at the upper surface of the injection port plate 125. The lower electrode input terminal 141 is connected to the lower electrode wiring pattern 132a. Also, an upper electrode input terminal 142 is formed at the upper surface of the injection port plate 125. The upper electrode input terminal 142 is connected to the upper electrode wiring pattern 133a.

The lower electrode input terminal 141 and the upper electrode input terminal 142 are connected to an external device that drives the actuator unit 130. Consequently, the actuator unit 130 is driven by drive voltage applied between the lower electrode input terminal 141 and the upper electrode input terminal 142 via the external device.

<Structure of Dispensing Apparatus>

Figure 6A:
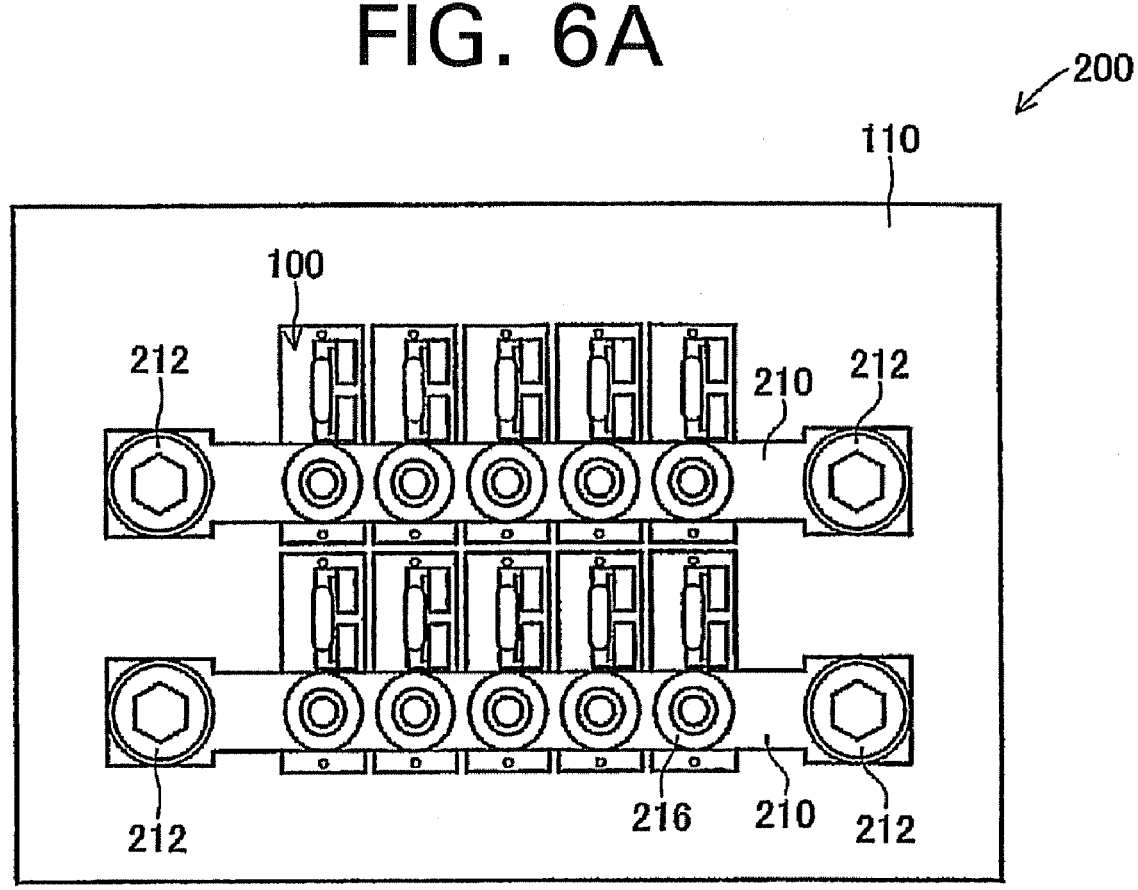
FIG. 6A is a plan view showing a general structure of a dispensing apparatus having the micropipette shown in FIG. 3.
Figure 6B:
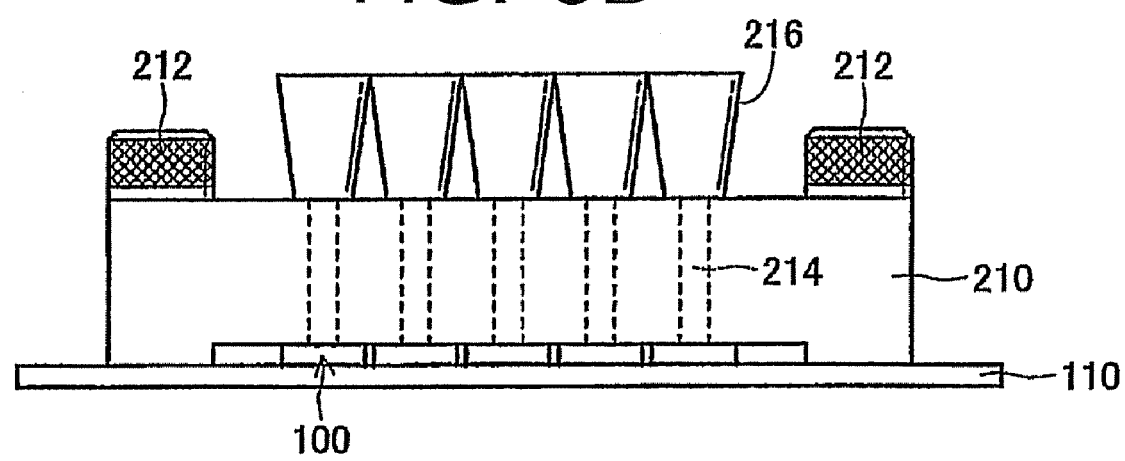
FIG. 6B is a side view of the dispensing apparatus.
Figure 7:
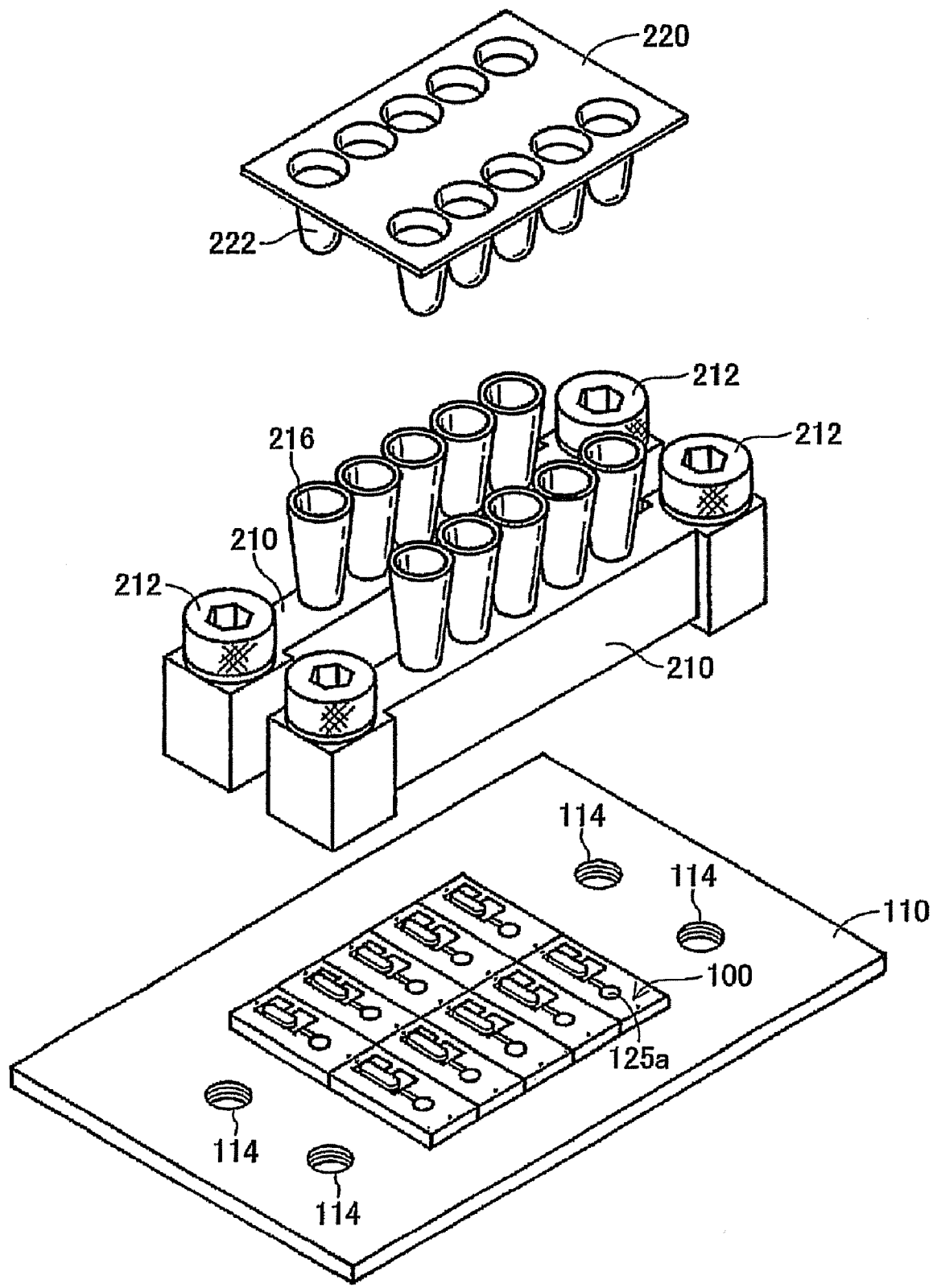
FIG. 7 is an exploded perspective view of the dispensing apparatus shown in FIG. 6.

Next, a dispensing apparatus 200 having the micropipette 100 with the above-stated structure will be described in detail. FIGS. 6A and 6B illustrate the structure of the dispensing apparatus 200. Specifically, FIG. 6A is a plan view of the dispensing apparatus 200, and FIG. 6B is a side view of the dispensing apparatus 200. FIG. 7 is an exploded perspective view of the dispensing apparatus 200.

As shown in FIG. 6A, the dispensing apparatus 200 includes a plurality (10 in the drawing) of micropipettes 100 arranged in two dimensions. All the micropipettes 100 have a common nozzle plate 110, the construction of which has already been described above. The common nozzle plate 110 is a ceramic plate.

The dispensing apparatus 200 includes sample introduction members 210 for introducing the sample solution to the respective sample injection ports 125a of the micropipettes 100 (see FIG. 5). As shown in FIGS. 6A and 6B, the sample introduction members 210 are connected to the upper surfaces of the micropipettes 110 arranged in the two dimensions. As shown in FIG. 7, the sample introduction members 210 are fixed to the upper surface of the nozzle plate 110 by means of threaded holes 114 formed in the nozzle plate 110 and fixing bolts 212.

Referring to FIG. 6B, sample injection channels 214, which are constructed in the shape of a through-hole, are formed in each sample introduction member 210. The openings at the lower ends of the sample injection channels 214 are connected to the corresponding sample injection ports 125a of the micropipettes 100 (see FIG. 5). Also, the openings at the upper ends of the sample injection channels 214 are connected to the lower ends of introduction tubes 216, which are constructed in the shape of a trumpet whose diameter gradually increases upward.

Referring to FIG. 7, the plural introduction tubes 216 arranged in two dimensions are disposed and constructed such that the introduction tubes 216 are coupled with plural sample storage portions 222, which are formed at a cartridge 220 that stores a sample solution, while the sample storage portions 222 protrude downward from the cartridge 220. The cartridge 220 is formed by injection molding of a soft synthetic resin. The cartridge 220 is constructed such that openings are formed at the bottoms of the sample storage portions 222 using a needle, and therefore, the sample solution stored in the sample storage portions 222 is introduced into the introduction tubes 216, whereby different kinds of sample solutions are supplied to the respective sample injection ports 125a.

Figure 8:
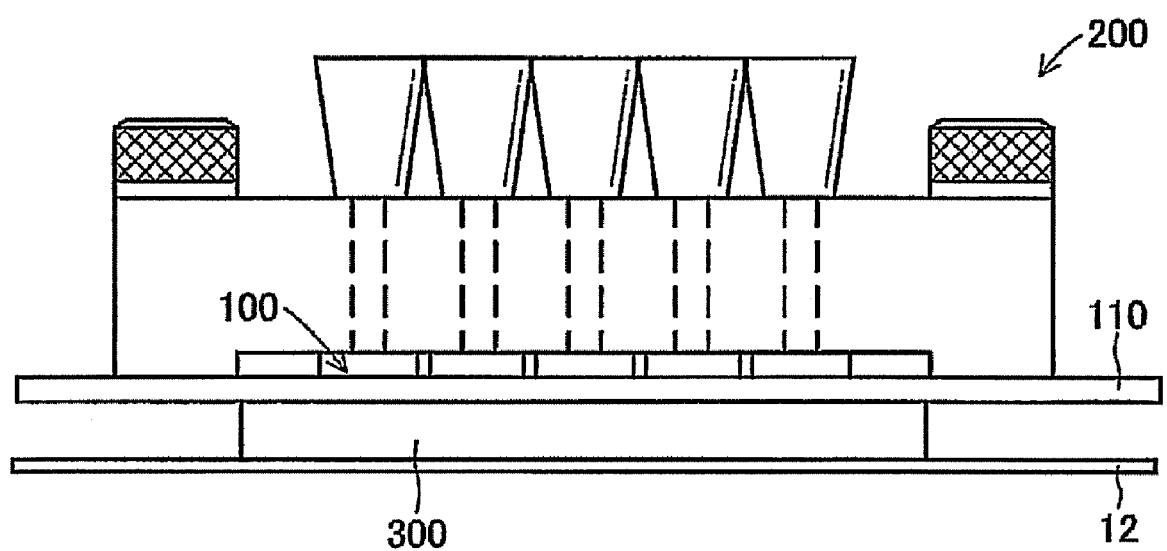
FIG. 8 is a side view illustrating a passage detection apparatus according one embodiment of the present invention, which is mounted in the dispensing apparatus shown in FIG. 6.
Figure 9:
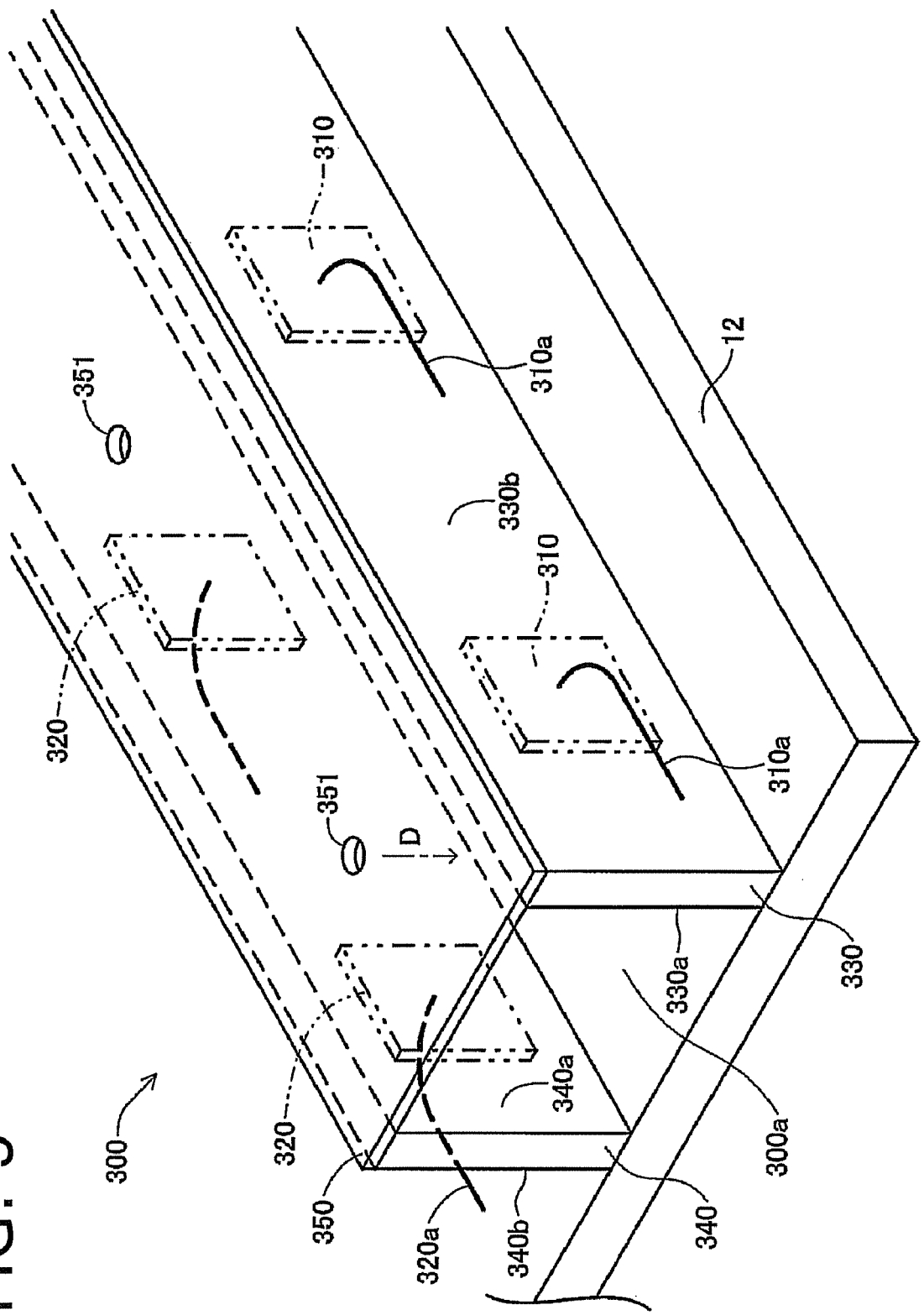
FIG. 9 is an enlarged perspective view showing the passage detection apparatus shown in FIG. 8.

General Structure of Passage Detection Apparatus According to a Preferred Embodiment Next, the general structure of a passage detection apparatus according to a preferred embodiment of the present invention will be described in detail. FIG. 8 is a side view illustrating a passage detection apparatus 300 according to the present embodiment mounted between the nozzle plate 110, having sample solution ejection ports, of the dispensing apparatus 200 and the DNA chip substrate 12 constituting the DNA chip 10 (see FIG. 1). FIG. 9 is an enlarged perspective view of the passage detection apparatus 300 according to the present embodiment.

Referring to FIG. 8, the passage detection apparatus 300 is configured as described below so as to be capable of detecting whether or not the sample solution is properly ejected to the DNA chip substrate 12 from each micropipette 100 at the dispensing apparatus 200.

Referring to FIG. 9, the passage detection apparatus 300 has a pair of detection units 310 and 320. The detection unit 310 is supported by a first substrate 330 that is vertical to the DNA chip substrate 12. A signal line 310a is electrically connected to the detection unit 310 for transmitting or receiving signals between the detection unit 310 and the above-mentioned external device (control device provided with a CPU, etc.). The detection unit 320 is supported by a second substrate 340 that is parallel to the first substrate 330, and arranged at the position corresponding to the detection unit 310 supported by the first substrate 330. A signal line 320a is electrically connected to the detection unit 320 for transmitting or receiving signals between the detection unit 320 and the above-mentioned external device.

A pair of detection units 310 and 320 is configured to receive the input of the signal from the external device through the signal lines 310a and/or 320a, and to output the signal to the external device through the signal lines 310a and/or 320a according to the state (the propagation state of ultrasonic wave or dielectric constant) in the space formed between both of them. Examples applicable to the detection units 310 and 320 include a pair of plate electrodes that can form a virtual capacitor for detecting the change in the dielectric constant, a piezoelectric/electrostrictive element that can generate a vibration according to the inputted signal and generate an output signal according to the inputted vibration, or the like. The detection units 310 and 320 may include a power supply, pulse generating source, etc. that supplies a predetermined DC voltage or a pulse voltage to the virtual capacitor or the piezoelectric/electrostrictive element.

An aperture plate having a thin plate-like shape is attached at the upper ends of the first substrate 330 and the second substrate 340. The aperture plate 350 is formed with an aperture 351, which is a through-hole through which micro drops of the sample solution ejected from the micropipette 100 (see FIG. 8) can pass. Plural apertures 351 are arranged and formed so as to correspond to the arrangement in two dimensions (see FIGS. 6 and 7) of the plural micropipettes 100 described above. The aperture 351 is formed in such a manner that the center of the aperture 351 viewed in a plane is positioned between the pair of opposite detection units 310 and 320 and positioned on the straight line linking the center of the detection unit 310 and the center of the detection unit 320. Specifically, the aperture 351 is formed such that, when the flight direction of the micro drop of the sample solution coincides with the predetermined direction (the direction of D in the figure), the micro drop passes through the aperture 351 and flies immediately below the aperture 351.

The space enclosed by the inner surface 330a, which is the surface facing the second substrate 340, of the first substrate 330 and the inner surface 340a, which the surface facing the first substrate 330, of the second substrate 340, which space is below the aperture plate 350, forms the specific space 300a through which the micro drops of the sample solution pass.

The signal line 310a connected to the detection unit 310 is arranged at the outside of the outer surface 330b, which is the surface reverse to the inner surface 330a, of the first substrate 330. Similarly, the signal line 320a connected to the detection unit 320 is arranged at the outside of the outer surface 340b, which is the surface reverse to the inner surface 340a, of the second substrate 340.

As described above, the passage detection apparatus 300 according to the present embodiment is configured to detect the change in the state (electrostatic capacitance and/or propagation state of ultrasonic wave), caused by the passage of the micro drops of the sample solution, in the specific space 300a by the detection units 310 and 320 arranged so as to enclose the specific space 300a, and to output the detected result through the signal lines 310a and/or 320a.

The passage detection apparatus 300 according to the present embodiment is configured such that the detection unit 310 faces the inner surface 330a of the first substrate 330, and the detection unit 320 faces the inner surface 340a of the second substrate 340. Specifically, when the volume of the micro drop is extremely small (e.g., picoliter order), for example, the detection units 310 and 320 are arranged so as to face the specific space 300a in order to detect the passage of the micro drop or the size (volume) thereof with high sensitivity.

Alternatively, the passage detection apparatus 300 is configured such that the detection unit 310 is exposed to the outer surface 330b of the first substrate 330 and the detection unit 320 is exposed to the outer surface 340b of the second substrate 340. Specifically, when the micro drop has conductivity, the detection units 310 and 320 are arranged at the outside of the specific space 300a in order that fault (short-circuit between the electrodes or corrosion) is not generated on the detection units 310 and 320 due to the deposition of the micro drop.

Further, the passage detection apparatus according to the present embodiment can be configured such that the detection unit 310 is exposed to the outer surface 330b of the first substrate 330 and the detection unit 320 is exposed to the inner surface 340a of the second substrate 340.

Moreover, the passage detection apparatus according to the present embodiment can be configured such that the detection unit 310 is exposed to the inner surface 330a of the first substrate 330 and the detection unit 320 is exposed to the outer surface 340b of the second substrate 340.

The arrangement relationship between the detection units 310 and 320 and the first and second substrates 330 and 340 can appropriately be selected according to the property of the micro drop (physical properties such as volume, weight, electrical conductivity, charging amount, etc.; chemical properties such as pH, corrosivity; moving speed; ejection cycle, etc.), the width of the specific space 300a (the distance between the inner surface 330a of the first substrate 330 and the inner surface 340a of the second substrate 340), the structures of the detection units 310 and 320, and the like.

Embodiments of Structure of Detection Unit

Next, the detail of the specific structure of the passage detection apparatus 300, i.e., the embodiments of the structure of the detection units 310 and 320 will be explained below.

Embodiment 1

Figure 10A:
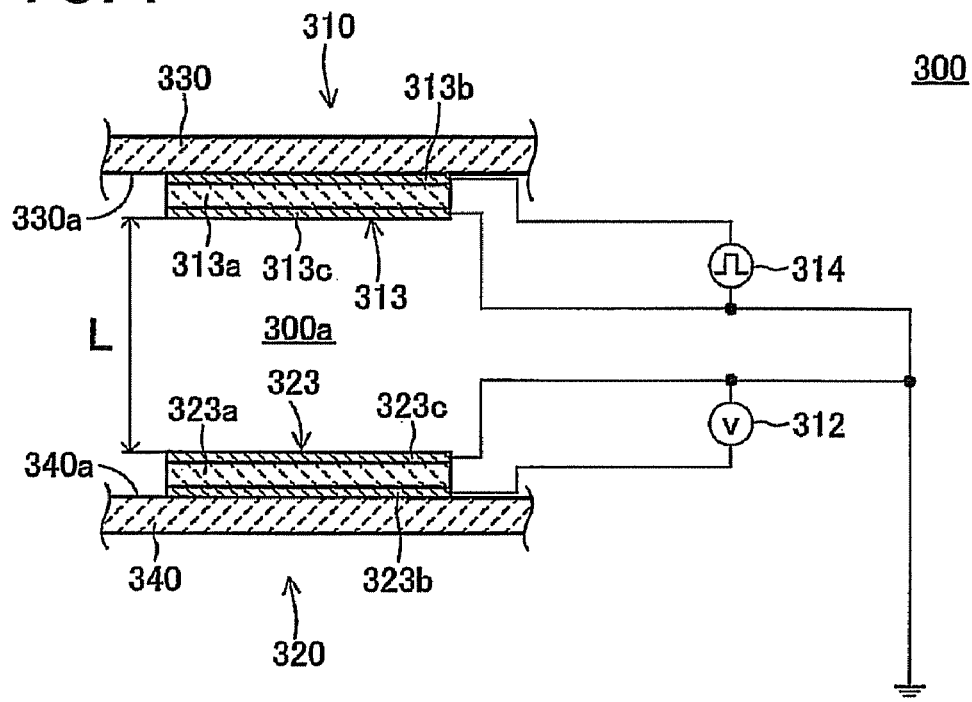
FIG. 10A is an enlarged sectional view showing the structure of a first embodiment of the passage detection apparatus shown in FIG. 9.
Figure 10B:
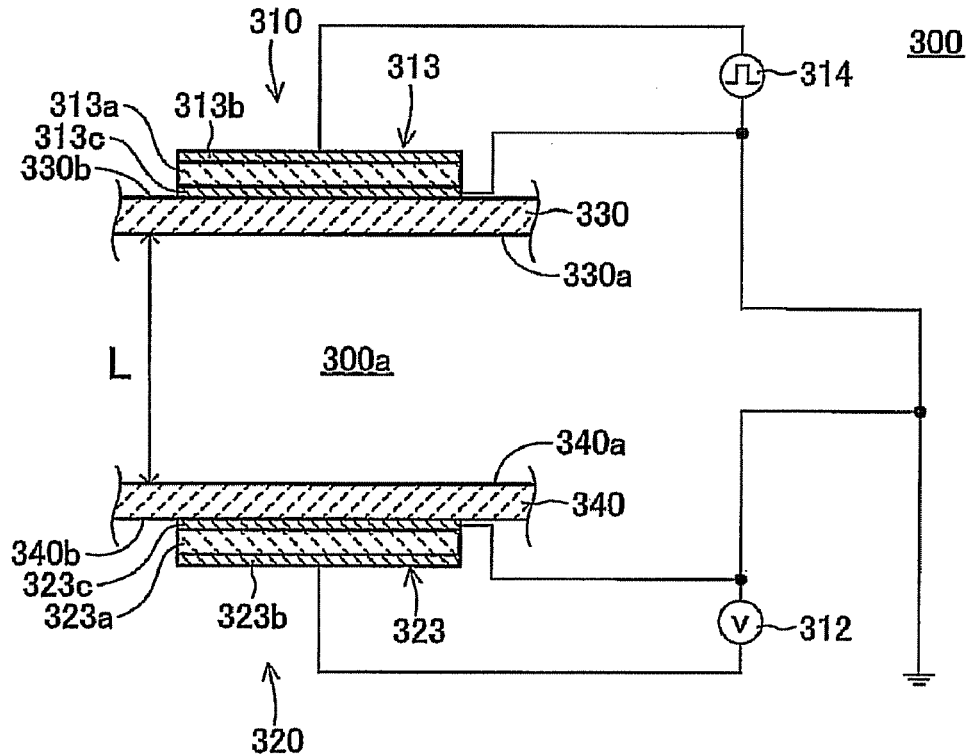
FIG. 10B is an enlarged sectional view showing the structure of a modification of the passage detection apparatus shown in FIG. 10A.

FIGS. 10A and 10B are enlarged sectional views showing a first embodiment of the structure of the detection units 310 and 320. In this embodiment, the detection units 310 and 320 are comprised of a piezoelectric/electrostrictive element.

Specifically, a first piezoelectric/electrostrictive element 313 constituting the detection unit 310 is comprised of a first dielectric layer 313a, a drive electrode 313b, and a first reference electrode 313c. The first dielectric layer 313a is formed from a thin plate of a piezoelectric/electrostrictive material (PZT, or the like) showing a piezoelectric effect and inverse piezoelectric effect. The drive electrode 313b and the first reference electrode 313c are made of a metallic film formed at both surfaces of the first dielectric layer 313a. The first piezoelectric/electrostrictive element 313 is formed integral with the first substrate 330 in such a manner that the coating layer, which is the base of the first dielectric layer 313a, the drive electrode 313b, and the first reference electrode 313c, is formed on the first substrate 330, and then sintered.

A second piezoelectric/electrostrictive element 323 constituting the detection unit 320 is comprised of a second dielectric layer 323a, a signal output electrode 323b, and a second reference electrode 323c. The second piezoelectric/electrostrictive element 323 has the structure same as that of the first piezoelectric/electrostrictive element, and is also formed integral with the second substrate 340.

An output terminal of a high voltage of a pulse generating source 314 that generates a pulse signal is connected to the drive electrode 313b of the first piezoelectric/electrostrictive element 313. The first reference electrode 313c is grounded. The first piezoelectric/electrostrictive element 313 is configured to produce a vibration by applying a voltage in the form of a pulse between the drive electrode 313b and the first reference electrode 313c from the pulse generating source 314. Specifically, the first piezoelectric/electrostrictive element 313 functions as a vibration generating source. The detection unit 310 is configured such that ultrasonic wave is propagated to the medium (air) in the specific space 300a by the vibration of the first piezoelectric/electrostrictive element 313.

The second piezoelectric/electrostrictive element 323 is configured to generate a voltage between the signal output electrode 323b and the second reference electrode 323c according to stress externally applied. A voltmeter 312 is connected to the second piezoelectric/electrostrictive element 323 for acquiring the voltage between the signal output electrode 323b and the second reference electrode 323c. The second reference electrode 323c is grounded. The second piezoelectric/electrostrictive element 323 is configured such that the second substrate 340 is vibrated due to the propagation of the ultrasonic wave to the second substrate 340 through the medium (air) in the specific space 300a, and the voltage is generated at both ends of the voltmeter 312 according to the stress applied to the second piezoelectric/electrostrictive element 323 by the vibration of the second substrate 340. Specifically, the second piezoelectric/electrostrictive element 320 constituting the detection unit 320 is configured as a sensor unit that can generate an output according to the vibration propagating through the medium in the specific space 300a from the first piezoelectric/electrostrictive element 313 (vibration generating source).

As described above, the passage detection apparatus according to the present embodiment is configured to detect the change in the propagation state of the ultrasonic wave in the specific space 300a on the basis of the change in the voltage at both ends of the voltmeter 312 so as to determine whether the micro drop of the sample solution passes through the specific space 300a or not or the volume of the micro drop.

In the present embodiment, the first piezoelectric/electrostrictive element 313 and the second piezoelectric/electrostrictive element 323 are arranged so as to form the specific space 300a between the first reference electrode 313c and the second reference electrode 323c. Specifically, the first piezoelectric/electrostrictive element 313 is arranged in such a manner that the first reference electrode 313c is closer to the specific space 300a compared to the drive electrode 313b. The second piezoelectric/electrostrictive element 323 is arranged in such a manner that the second reference electrode 323c is closer to the specific space 300a compared to the signal output electrode 323b.

As described above, the specific space 300a is arranged so as to be sandwiched between the grounded first reference electrode 313c and the grounded second reference electrode 323c in the passage detection apparatus 300 according to the present embodiment. Specifically, the passage detection apparatus 300 is configured to prevent the generation of the electric field in the specific space 300a, whereby it is prevented that the flight route of the micro drop is curved due to the electric field, when the micro drop of the sample solution is electrostatically charged.

The width L of the specific space 300a is set to satisfy the following equation, supposing that the wavelength of the vibration propagating through the medium (air, etc.) in the specific space 300a is λ, and n is a natural number.

$$L = n\lambda$$

In the structure shown in FIG. 10A, the first piezoelectric/electrostrictive element 313 is formed on the inner surface 330a of the first substrate 330. The second piezoelectric/electrostrictive element 323 is formed on the inner surface 340a of the second substrate 340. Specifically, the first piezoelectric/electrostrictive element 313 and the second piezoelectric/electrostrictive element 323 are arranged to face the specific space 300a.

In the structure shown in FIG. 10B, the first piezoelectric/electrostrictive element 313 is provided on the outer surface 330b of the first substrate 330. The second piezoelectric/electrostrictive element 323 is provided on the outer surface 340b of the second substrate 340. Specifically, the first piezoelectric/electrostrictive element 313 and the second piezoelectric/electrostrictive element 323 are arranged at the outside of the specific space 300a (so as not to be exposed to the specific space 300a).

<Circuit Configuration for Determination of Passage of Object>

Next, the circuit configuration for determining the ejection state of the micro drop of the sample solution from the micropipette 100 (see FIG. 8) by using the structure in the first embodiment will be explained with reference to FIG. 11.

A determination/control section 360 includes a CPU, etc. for controlling the overall operation of the present apparatus. The determination/control section 360 is connected to the detection unit 320, drive voltage applying section 370, and actuator driver 380.

The drive voltage applying section 370 includes the pulse generating source 314 shown in FIGS. 10A and 10B for applying a drive voltage to the detection unit 310 (the first piezoelectric/electrostrictive element 313 in FIGS. 10A and 10B). The determination/control section 360 controls the drive voltage applying section 370, thereby applying a drive voltage having an arbitrary waveform to the detection unit 310.

The determination/control section 360 is connected to the detection unit 320 (the second piezoelectric/electrostrictive element 323 in FIGS. 10A and 10B) for receiving an output signal from the detection unit 320. Specifically, the determination/control section 360 is configured to include the voltmeter 312 in FIGS. 10A and 10B. The determination/control section 360 receives an output generated from the detection unit 320 and determines the ejecting state of the micro drop of the sample solution on the basis of the output.

The actuator driver 380 is connected to the lower electrode input terminal 141 and the upper electrode input terminal (see FIG. 5) in the actuator unit 130. The determination/control section 360 is configured to control the drive (i.e., the ejection of the micro drop of the sample solution) of the actuator unit 130 through the actuator driver 380.

Description of Operation of Apparatus According to Embodiment

Next, the operation of the apparatus with the above-mentioned structure according to the embodiment will be described with reference to the drawings.

<<Manufacturing Process of DNA Chip>>

First, the manufacturing process of the DNA chip 10 shown in FIG. 1 will be described. The manufacturing process includes a pre-treatment process of forming a sample support layer 14 (see FIG. 2), which is a poly-L-lysine layer, on the surface of the DNA chip substrate 12, a sample manufacturing process of manufacturing a sample solution containing DNA pieces, and a supply process of supplying the manufactured sample solution onto the DNA chip substrate 12.

The pre-treatment process is carried out as follows. First, the DNA chip substrate 12 is soaked in a predetermined alkali solution at room temperature for at least two hours. As the alkali solution, for example, there may be used a solution obtained by dissolving NaOH in distilled water, adding ethanol in the mixture, and stirring the mixture until the mixture becomes fully transparent. After that, the DNA chip substrate 12 is taken out of the alkali solution, and is then washed in distilled water. Subsequently, the DNA chip substrate 12 is soaked in a poly-L-lysine solution manufactured by adding poly-L-lysine in distilled water for approximately one hour. After that, the DNA chip substrate 12 is taken out of the poly-L-lysine solution, and the poly-L-lysine solution remaining on the DNA chip substrate 12 is removed by centrifugal separation. Subsequently, the DNA chip substrate 12 is dried at 40° C. for approximately 5 minutes. In this way, a DNA chip substrate 12 having the poly-L-lysine sample support layer 14 formed on the surface thereof is obtained.

The sample manufacturing process includes an amplifying process of amplifying the base sequence of the DNA pieces, using polymerase chain reaction (PCR), to obtain a PCR product, a powder producing process of drying the obtained PCR product to obtain DNA powder, and a mixing process of dissolving the obtained DNA powder in a buffer solution. In the powder producing process, first, sodium acetate of 3 M (=3 mol/l) and isopropanol are added to the PCR product, and the mixture is left for a few hours. After that, the solution is centrifugally separated, and therefore, the DNA pieces are precipitated. The precipitated DNA pieces are rinsed using ethanol, are centrifugally separated, and are then dried. As a result, DNA powder is produced. In the mixing process, a Tris-EDTA (TE) buffer solution is added to the DNA powder, and the mixture is left for a few hours until the DNA powder is fully dissolved in the buffer solution. As a result, a sample solution is prepared. The concentration of the sample solution prepared at this step is 1 to 10 μg/μl.

The sample solution obtained as described above is stored in the sample storage portions 222 of the cartridge 220 shown in FIG. 7. Since the cartridge 220 is mounted to the dispensing apparatus 200 shown in FIG. 6, the sample solution is supplied into the respective micropipettes 100 in the dispensing apparatus 200. And the micro drops of the sample solution are ejected toward the DNA chip substrate 12 (see FIG. 1) from the respective micropipettes 100, and therefore, the micro drops of the sample solution are supplied onto the DNA chip substrate 12. As a result, plural micro spots S of the sample solution are formed on the DNA chip substrate 12 in a predetermined array. In this way, the DNA chip 10 is manufactured.

Here, it is difficult to observe the micro drops of the sample solution with the naked eye. For this reason, the determination as to whether or not the micro drops of the sample solution are properly formed on the DNA chip substrate 12 in the predetermined array (whether the ejecting operation is not correctly carried out, for example, the micro drops are not ejected, in one or more specific micropipettes 100) cannot be performed with the naked eye. On the other hand, it is possible to determine whether the micro drops are not ejected by scanning the ejection route of the micro drops with a laser beam. However, the construction of an apparatus for determining whether the ejecting operation is not correctly carried out in the respective micropipettes 100 by scanning the laser beam as described above is very expensive.

On the contrary, the determination as to whether the ejecting operation is not correctly carried out in the respective micropipettes 100 of the dispensing apparatus 200 is accomplished using the passage detection apparatus 300 according to the preferred embodiment of the present invention as shown in FIG. 8. As described above, the structure of the passage detection apparatus 300 is very simple, and therefore, the manufacturing costs of the passage detection apparatus 300 are very low. Although the structure of the passage detection apparatus 300 is very simple as described above, it is possible for the passage detection apparatus 300 to accurately perform the determination as to whether the ejecting operation is not correctly carried out.

Description of Object Passage Determination Operation According Embodiment

Next, the determining operation of the ejection state of the micro drops of the sample solution in the micropipettes 100 using the passage detection apparatus 300 according to this embodiment will be described in detail with reference to the drawings.

As shown in FIG. 8, the passage detection apparatus 300 is disposed below the nozzle plate 110 of the micropipettes 100. Specifically, the passage detection apparatus 300 is arranged at the lower part of the dispensing apparatus 200 such that the nozzle plate 110 faces the aperture plate 350 (see FIG. 9) of the passage detection apparatus 300. The dispensing apparatus 200 is driven by an external device. Specifically, the actuator unit 130 (see FIG. 5) of each micropipette 100 mounted to the dispensing apparatus 200 is driven. Accordingly, micro drops of the sample solution are ejected from the respective micropipettes 100.

Here, the passage detection apparatus 300 is arranged in such a manner that the nozzle 112 (see FIG. 3) and the aperture 351 (see FIG. 9) are arranged on a straight line parallel to the flight direction D (see FIG. 9) of the micro drop from the nozzle 112. By virtue of this configuration, when the ejecting direction is not appropriate (the ejecting direction is not parallel to the predetermined flight direction D shown in FIG. 9) even if the micro drops are ejected from the micropipettes 100, the micro drops collide with the aperture plate 350 so as not to pass through the aperture 351.

Referring to FIG. 9, when the micro drops are ejected parallel to the predetermined flight direction D, the micro drops pass the aperture 351. The micro drops passing through the aperture 351 enter the specific space 300a. Accordingly, the state (propagation state of ultrasonic wave, dielectric constant, etc.) of the inside of the specific space 300a changes. The degree of the change is different depending upon the property of the micro drops. Thus, the state of the inside of the specific space 300a is detected by the detection units 310 and 320, whereby the passage state of the micro drops in the specific space 300a can be detected. Specifically, whether the micro drops enter the specific space 300a or not, and the size of the micro drops are determined.

Description of Operation of Object Passage Determination in First Embodiment

Referring to FIGS. 10A, 10B and 11, the determination/control section 360 controls the drives of the actuator unit 130 and the detection unit 310 (first piezoelectric/electrostrictive element 313) in such a manner that the drive of the detection unit 310 (first piezoelectric/electrostrictive element 313) is synchronous with the drive of the actuator unit 130. With this configuration, the first piezoelectric/electrostrictive element 313 and the first substrate 330 vibrate, whereby ultrasonic wave is generated. The ultrasonic wave propagates through the medium in the specific space 300a to reach the second substrate 340. Thus, the second substrate 340 is vibrated. By the vibration of the second substrate 340, a voltage is generated on the detection unit 320 (second piezoelectric/electrostrictive element 323).

Figure 12:
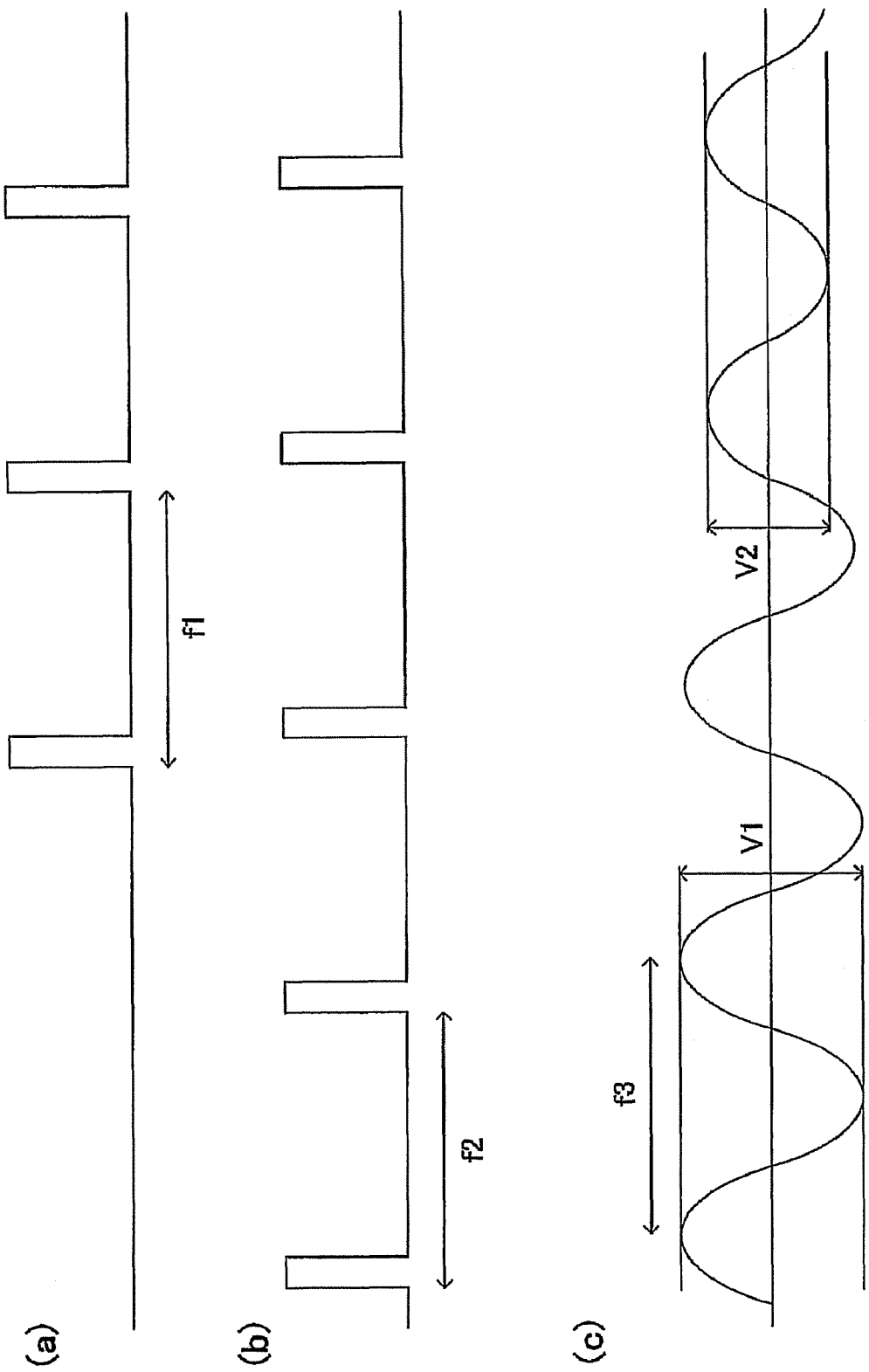
FIG. 12 is a signal chart showing the state of a drive control of the dispensing apparatus and the state of the detection of the passage of the object at the determination/control unit shown in FIG. 11.

Referring to FIG. 12, for example, the actuator unit 130 (see FIG. 11) is periodically driven by a pulse wave having a predetermined cycle (frequency f1) as illustrated in a time chart (a). The drive pulse of the actuator unit 130 is generated synchronous with the pulse wave having the predetermined cycle (frequency f2) for driving the detection unit 310 (first piezoelectric/electrostrictive element 313 in FIGS. 10A and 10B) as illustrated in a time chart (b). In this case, the frequency f1 is generally equal to the frequency f2. Further, the frequency f2 is a resonant frequency of the detection unit 310 (first piezoelectric/electrostrictive element 313 in FIGS. 10A and 10B). Accordingly, a waveform illustrated in a time chart (c) is generated on the detection unit 320 (second piezoelectric/electrostrictive element 323 in FIGS. 10A and 10B). This waveform is generated with a predetermined cycle (frequency f3). In this case, the frequency f3 is generally equal to the frequency f1 and f2.

The vibration state of the second substrate 340 changes according to the propagating state of the vibration in the specific space 300a. The propagating state of the vibration in the specific space 300a differs depending upon the presence of the micro drops in the specific space 300a or the size of the micro drops. Therefore, whether the micro drops enter the specific space 300a or not and the size of the micro drops are determined, through the detection of the change in the propagating state in the specific space 300a by the detection unit 320.

Referring to FIG. 12, a voltage Vpp (peak-to-peak voltage) is V1 at the output waveform (see the time chart (c)) of the detection unit 320 before the actuator unit 130 (see FIG. 11) is driven. On the other hand, the voltage Vpp (peak-to-peak voltage) becomes V2, which is smaller than V1, at the output waveform (see the time chart (c)) of the detection unit 320 after the actuator unit 130 (see FIG. 11) is driven and when the micro drops enter the specific space 300a (see FIGS. 10A and 10B). Thus, the output voltage of the detection unit 320 is acquired, whereby whether the micro drops enter the specific space 300a or not and the size of the micro drops are determined.

Referring again to FIGS. 10A and 10B, the specific space 300a is sandwiched between the grounded first reference electrode 313c and the grounded second reference electrode 323c, whereby the generation of the electric field in the specific space 300a is suppressed according to the first embodiment. Therefore, it is prevented that the flight route of the micro drop is curved by the electric field, when the micro drop of the sample solution is electrostatically charged, whereby the ejection state is surely be detected.

According to the first embodiment, the width L of the specific space 300a is set to satisfy the following equation, supposing that the wavelength of the vibration propagating through the medium (air, etc.) in the specific space 300a is λ, and n is a natural number.

$$L = n\lambda$$

Therefore, the vibration in the specific space 300a is efficiently be propagated. Consequently, power saving of the first piezoelectric/electrostrictive element 313 constituting the vibration generating source is possible. Further, the sensitivity of the second piezoelectric/electrostrictive element 323 constituting the sensor unit can be enhanced.

In the structure shown in FIG. 10A, the first piezoelectric/electrostrictive element 313 and the second piezoelectric/electrostrictive element 323 are arranged at the inside of the specific space 300a. With this structure, the sensitivity of the second piezoelectric/electrostrictive element 323 constituting the sensor unit 320 for receiving ultrasonic wave can further be enhanced. Moreover, the passage detection apparatus 300 can further be miniaturized, whereby the passage of drop having more micro size can satisfactorily be detected.

In the structure in FIG. 10B, the first piezoelectric/electrostrictive element 313 and the second piezoelectric/electrostrictive element 323 are arranged at the outside of the specific space 300a (so as not to be exposed to the specific space 300a). Specifically, the inner wall surface of the specific space 300a is made of the surface of the dielectric member. Therefore, this structure can prevent that fault occurs on the first piezoelectric/electrostrictive element 313 and the second piezoelectric/electrostrictive element 323 due to the deposition of the sample solution onto the first piezoelectric/electrostrictive element 313 and the second piezoelectric/electrostrictive element 323.

Another Embodiment of Structure of Detection Unit

Next, another embodiment of the structure of the detection units 310 and 320 will be explained below.

Embodiment 2

Figure 13:
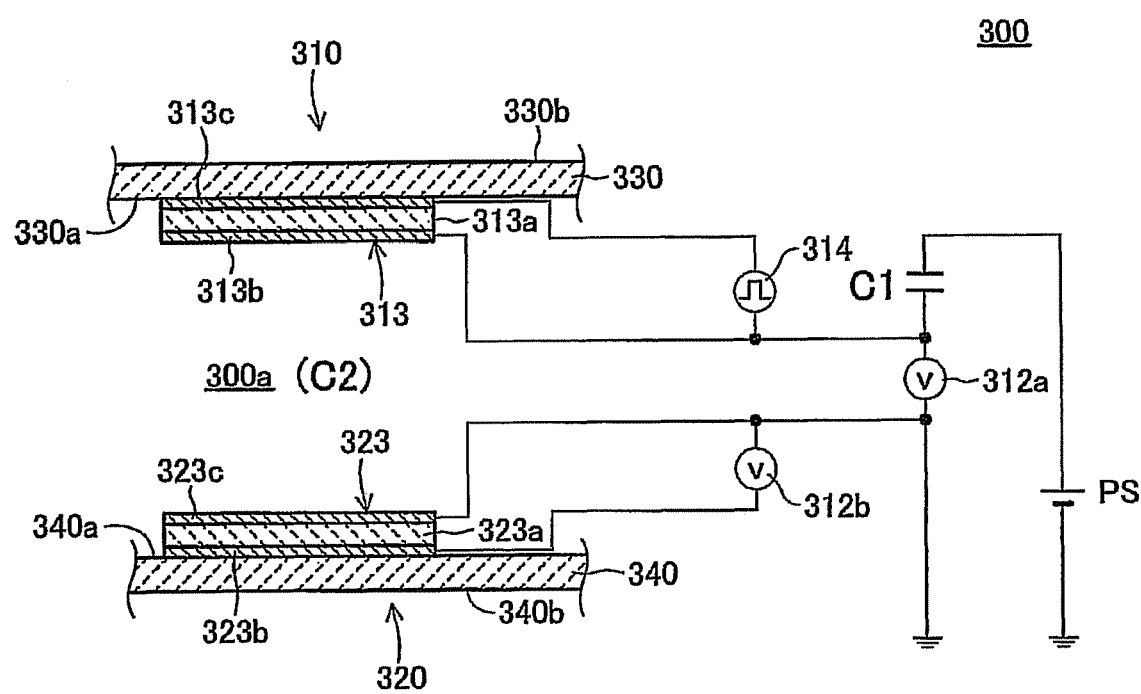
FIG. 13 is an enlarged sectional view showing the second embodiment of the passage detection apparatus shown in FIG. 9.

FIG. 13 is an enlarged sectional view showing the structure of the detection units 310 and 320 according to the second embodiment. The passage detection apparatus 300 according to this embodiment is configured to determine whether the micro drop of the sample solution passes through the specific space 300a or not or the volume of the micro drop on the basis of the change in the dielectric constant (electrostatic capacitance of a virtual capacitor) in the specific space 300a and the propagation state of the ultrasonic wave in the specific space 300a. The specific structure of the passage detection apparatus 300 according to the present embodiment will be described below.

Like the aforesaid first embodiment, a pulse generating source 314 is connected to the first piezoelectric/electrostrictive element 313 constituting the detection unit 310 in the present embodiment. A voltmeter 312b is connected to the second piezoelectric/electrostrictive element 323 constituting the detection unit 320.

The first piezoelectric/electrostrictive element 313 is arranged such that the drive electrode 313b is positioned at the side of the specific space 300a. The drive electrode 313b is connected to a DC power supply PS through a known capacitor C1 having electrostatic capacitance. The second piezoelectric/electrostrictive element 323 is arranged such that the second reference electrode 323c is positioned at the side of the specific space 300a. The second reference electrode 323c is grounded. The drive electrode 313b and the second reference electrode 323c are connected to a voltmeter 312a, wherein the voltage between the drive electrode 313b and the second reference electrode 323c is acquired by the voltmeter 312a. The voltmeter 312b is connected to the second piezoelectric/electrostrictive element 323 so as to acquire the voltage between the signal output electrode 323b and the second reference electrode 323c.

Specifically, in the present embodiment, a virtual capacitor C2 is formed between the electrodes, which are close to the specific space 300a, of the first and second piezoelectric/electrostrictive elements 313 and 323, wherein the electrostatic capacitance of the virtual capacitor C2 is changed according to the change in the dielectric constant in the specific space 300a (the presence of the object in the specific space 300a or the size of the object). Further, the virtual capacitor C2 is serially connected to the known capacitor C1. The partial voltage of the virtual capacitor C2, of the voltages at both ends of the DC power supply PS, can be acquired by the voltmeter 312a.

As described above, the passage detection apparatus 300 according to the present embodiment is configured to determine whether the micro drop of the sample solution passes through the specific space 300a or not or the volume of the micro drop on the basis of the change in the partial voltage of the virtual capacitor C2 formed between the drive electrode 313b of the first piezoelectric/electrostrictive element 313 and the second reference electrode 323c of the second piezoelectric/electrostrictive element 323, and the change in the output voltage by the second piezoelectric/electrostrictive element 323.

In the present embodiment, the circuit configuration shown in FIG. 11 can also be applied. In this case, the determination/control section 360 in FIG. 11 is configured to include the voltmeter 312a, voltmeter 312b, capacitor C3, and DC power supply PS in FIG. 13.

Description of Operation of Object Passage Determination in Second Embodiment

In the structure in the present embodiment, the drive control of the first piezoelectric/electrostrictive element 313 or the like or the passage of the micro object or the like can be determined as shown in FIG. 12 by using the circuit configuration shown in FIG. 11.

Referring to FIG. 13, when the first piezoelectric/electrostrictive element 313 constituting the detection unit 310 is driven at a predetermined timing, ultrasonic wave is generated according to the second embodiment like the first embodiment. This ultrasonic wave propagates through the medium in the specific space 300a to reach the second substrate 340. Accordingly, the second substrate 340 is vibrated. The vibration of the second substrate 340 causes a voltage at the second piezoelectric/electrostrictive element 323. The voltage generated at the second piezoelectric/electrostrictive element 323 is acquired by the voltmeter 312b.

According to the present embodiment, the change in the partial voltage of the virtual capacitor C2 formed between the drive electrode 313b of the first piezoelectric/electrostrictive element 313 and the second reference electrode 323c of the second piezoelectric/electrostrictive element 323 is acquired by the voltmeter 312a. Then, whether the micro drop of the sample solution passes through the specific space 300a or not or the volume of the micro drop can be determined on the basis of the output of the voltmeters 312a and 312b. For example, when an appropriate statistical process is carried out by the determination/control section 360 in FIG. 11 to the result of the detection on the basis of the output from the voltmeter 312a and the result of the detection on the basis of the voltmeter 312b, the passage of the object can be detected with higher reliability, regardless of the property of the object (size, chargeabililty, etc.).

Embodiment 3

Figure 14:
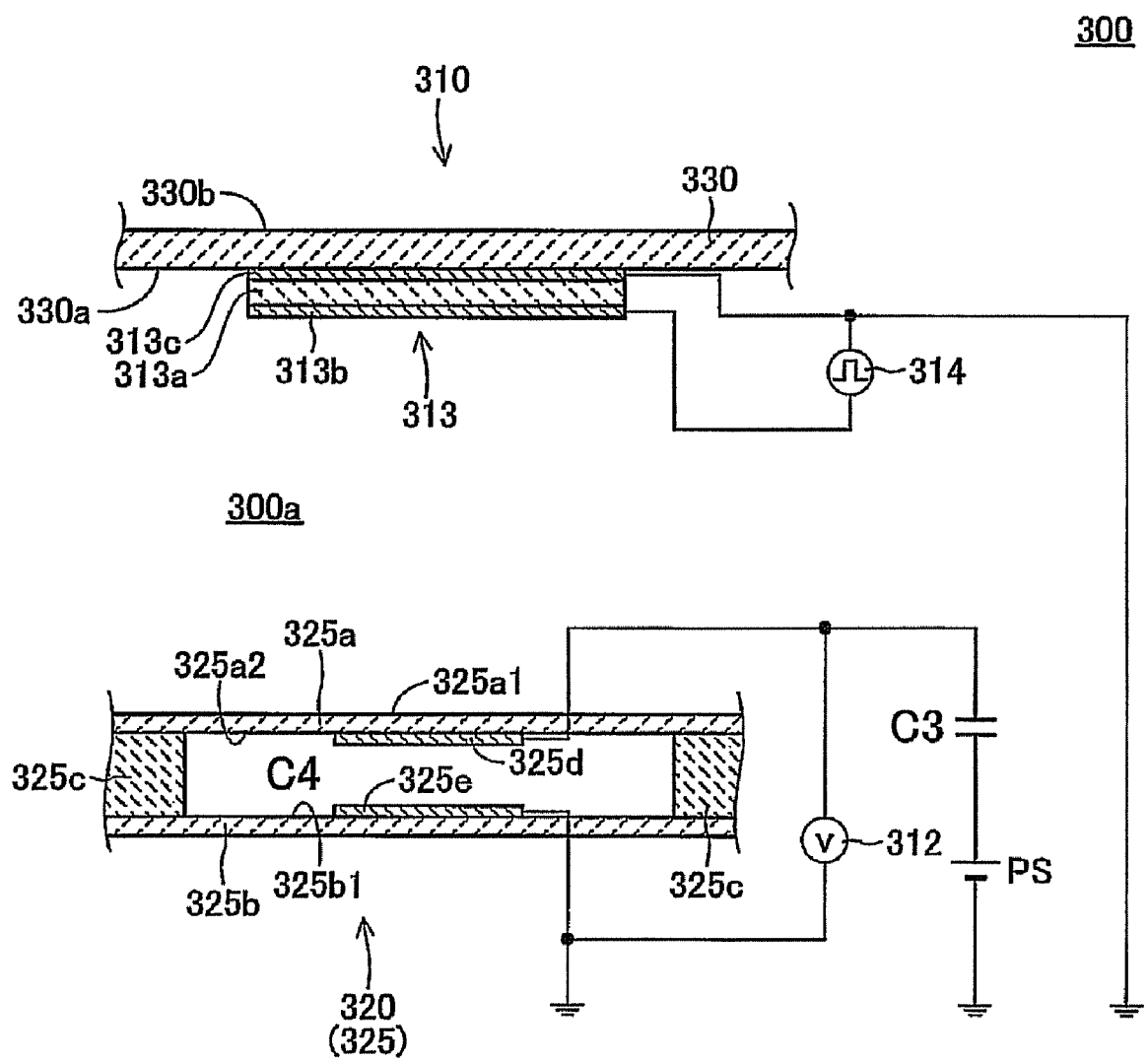
FIG. 14 is an enlarged sectional view showing the third embodiment of the passage detection apparatus shown in FIG. 9.

FIG. 14 is an enlarged sectional view showing the structure of the detection units 310 and 320 according to the third embodiment. In this embodiment, the detection unit 310 is comprised of the first piezoelectric/electrostrictive element 313 same as that in the first and second embodiments. In the present embodiment, the detection unit 320 is comprised of an electrostatic microphone 325, different from the first embodiment.

The electrostatic microphone 325 has a vibration plate 325a, support plate 325b, spacer 325c, first detection electrode 325d, and second detection electrode 325e, wherein a voltage according to applied external force is produced between the first detection electrode 325d and the second detection electrode 325e.

The vibration plate 325a is made of a dielectric layer having a thin plate shape, and is a member for constituting the outer wall enclosing the specific space 300a (a member corresponding to the second substrate 340 (see FIGS. 10A and 10B) in the aforesaid first embodiment). Specifically, the inner surface of the electrostatic microphone 325 facing the specific space 300a is made of the inner surface 325a1 of the vibration plate 325a. The support plate 325b is made of a dielectric layer having a thin plate shape. The support plate 325b is arranged so as to be parallel to the vibration plate 325a with a predetermined gap. The spacer 325c is a plate-like member formed with multiple through-holes, and is arranged between the vibration plate 325a and the support plate 325b so as to form a predetermined gap between the vibration plate 325a and the support plate 325b by the through-holes.

As described above, the vibration plate 325a is arranged to be bridged in the through-holes formed to the spacer 325c. The vibration plate 325a is arranged at the position opposite to the first piezoelectric/electrostrictive element 313 serving as the vibration generating source. The vibration plate 325a is configured to vibrate by the propagation of the vibration, generated from the first piezoelectric/electrostrictive element 313, through the medium in the specific space 300a.

The first detection electrode 325d is formed on the outer surface 325a2, which is the backside of the inner surface 325a1, of the vibration plate 325a. The first detection electrode 325d is connected to the DC power supply PS through a known capacitor C3 having electrostatic capacitance. The second detection electrode 325e is formed on the inner surface 325b1, which faces the vibration plate 325a, of the support plate 325b, and arranged parallel to the first detection electrode 325d. The second detection electrode 325e is grounded. The first detection electrode 325d and the second detection electrode 325e are connected to the voltmeter 312 so as to acquire the voltage between the first detection electrode 325d and the second detection electrode 325e.

Specifically, a virtual capacitor C4 is formed in the electrostatic microphone 325 by the first detection electrode 325d and the second detection electrode 325e. The virtual capacitor C4 is configured to change its electrostatic capacitance depending upon the change in the distance of the gap, caused by the vibration of the vibration plate 325a, between the first detection electrode 325d and the second detection electrode 325e. The virtual capacitor C4 is serially connected to the aforesaid known capacitor C3. The voltmeter 312 is connected to the first detection electrode 325d and the second detection electrode 325e in such a manner that the partial voltage of the virtual capacitor C4, of the voltages at both ends of the DC power supply PS, can be acquired by the voltmeter 312.

As described above, the electrostatic microphone 325 in this embodiment is configured to output a signal according to the vibrating state of the vibration plate 325a on the basis of the change in the partial voltage of the virtual capacitor C4. The passage detection apparatus 300 in the present embodiment is configured to determine whether or not the micro drop of the sample solution passes through the specific space 300a or the volume of the micro drop, through the detection of the propagation state of the ultrasonic wave in the specific space 300a on the basis of the change in the voltage at both ends of the voltmeter 312.

In the present embodiment, the circuit configuration shown in FIG. 11 can also be used. In this case, the determination/control section 360 in FIG. 11 is configured to include the voltmeter 312, capacitor C3, and DC power supply PS in FIG. 14.

Description of Operation of Object Passage Determination in Third Embodiment

Referring to FIG. 14, according to the structure of the third embodiment, when the first piezoelectric/electrostrictive element 313 constituting the detection unit 310 is driven at a predetermined timing, ultrasonic wave is generated.

In the present modification, the vibration plate 325a vibrates due to the ultrasonic wave propagated to the detection unit 320 through the medium in the specific space 300a. The distance of the gap between the first detection electrode 325d and the second detection electrode 325e changes (specifically, the electrostatic capacitance of the virtual capacitor C4 changes) by the vibration of the vibration plate 325a. With the change of the electrostatic capacitance of the virtual capacitor C4, the change in the partial voltage of the virtual capacitor C4 is acquired by the voltmeter 312. The state of the change in the partial voltage varies depending upon whether the micro drop enters the specific space 300a or not and the size of the micro drop as shown in FIG. 12(c). Consequently, whether the micro drop enters the specific space 300a or not and the size of the micro drop can be determined.

According to the configuration of the present embodiment, various materials can be selected as the material for the vibration plate 325a. For example, a film made of synthetic resin may be used as the vibration plate 325a. In this case, the first detection electrode 325d can also be formed easily into a thin film by the application of a metallized film. Accordingly, the whole rigidity of the vibration plate 325a and the first detection electrode 325d reduces, whereby the vibration plate 325a greatly vibrates due to a slight vibration of the medium in the specific space 300a. Therefore, the slight change of the vibration state of the medium can appear as the great change of the vibration state at the vibration plate 325a. Consequently, the sensitivity in detecting a passage of an object can further be enhanced.

Embodiment 4

Figure 15A:
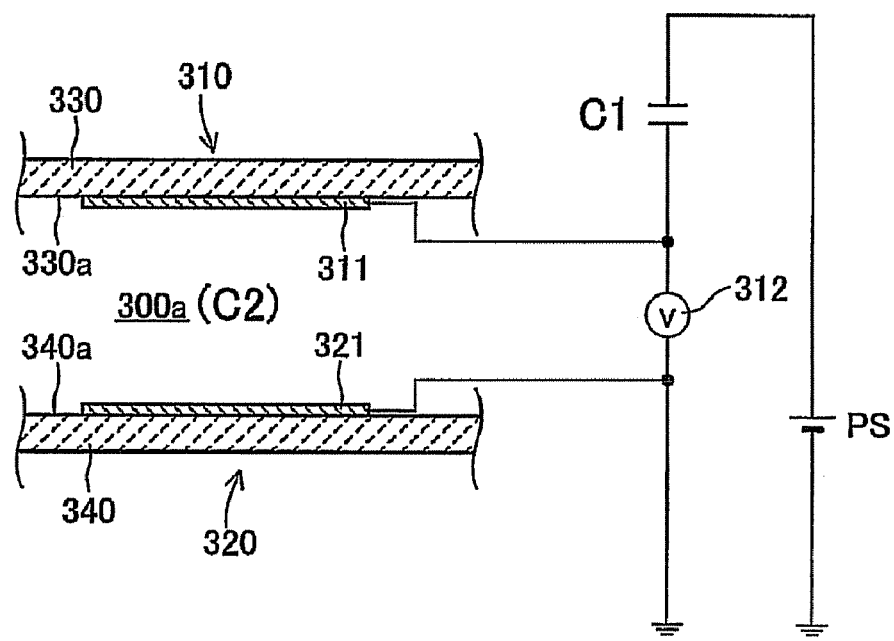
FIG. 15A is an enlarged sectional view showing the fourth embodiment of passage detection apparatus shown in FIG. 9.
Figure 15B:
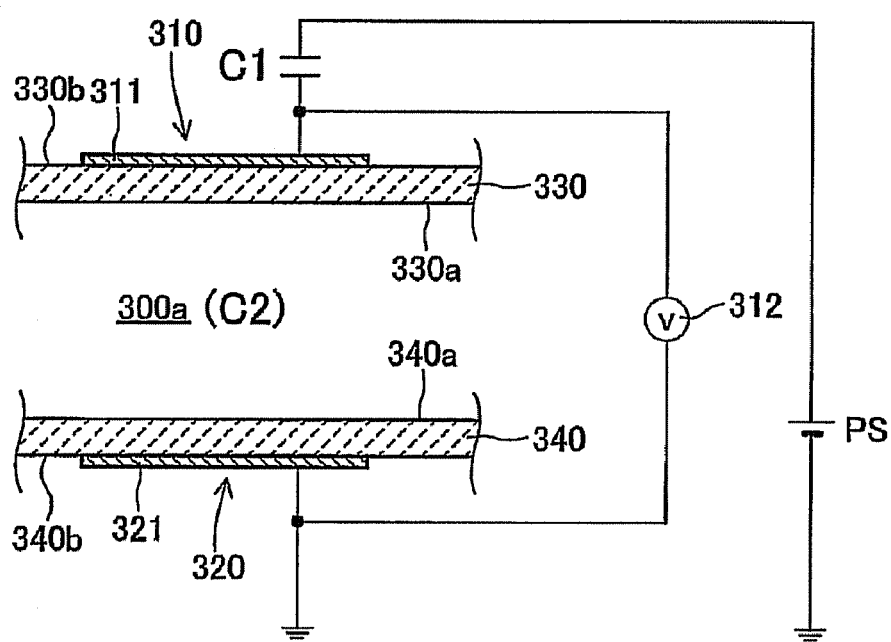
FIG. 15B is an enlarged sectional view showing the structure according to the modification of the passage detection apparatus shown in FIG. 15A.

FIGS. 15A and 15B are enlarged sectional views showing the structure of the detection units 310 and 320.

In the present embodiment, the detection unit 310 is comprised of a plate-like first electrode 311 supported on the first substrate 330. The first substrate 330 is comprised of a plate-like dielectric layer. The first electrode 311 is connected to a DC power supply PS through a known capacitor C1 having an electrostatic capacitance.

In the present embodiment, the detection unit 320 is comprised of a plate-like second electrode 321 supported on the second substrate 340. The second substrate 340 is comprised of a plate-like dielectric layer. The second electrode 321 is grounded, and arranged parallel to the first electrode 311 across the specific space 300a. The first electrode 311 and the second electrode 321 are connected to the voltmeter 312, and the voltage between the first electrode 311 and the second electrode 321 is acquired by the voltmeter 312.

Specifically, in the present embodiment, a pair of detection units 310 and 320 fowls a virtual capacitor C2, wherein the electrostatic capacitance of the virtual capacitor C2 is changed according to the change in the dielectric constant in the specific space 300a (the presence of the object in the specific space 300a or the size of the object), which is the space between the detection unit 310 and the detection unit 320. The virtual capacitor C2 is serially connected to the known capacitor C1. The voltmeter 312 is connected to the first electrode 311 and the second electrode 321 in such a manner that the partial voltage, of the voltages at both ends of the DC power supply PS, of the virtual capacitor C2 can be acquired b the voltmeter 312.

As described above, the passage detection apparatus 300 according to the present embodiment is configured to determine whether the micro drop of the sample solution passes through the specific space 300a or not or the volume of the micro drop on the basis of the change in the partial voltage of the virtual capacitor C2.

In the structure shown in FIG. 15A, the first electrode 311 is provided on the inner surface 330a of the first substrate 330. The second electrode 321 is provided on the inner surface 340a of the second substrate 340. Specifically, the first electrode 311 and the second electrode 321 are arranged to face the specific space 300a.

In the structure shown in FIG. 15B, the first electrode 311 is provided on the outer surface 330b of the first substrate 330. The second electrode 321 is provided on the outer surface 340b of the second substrate 340. Specifically, the first electrode 311 and the second electrode 321 are arranged at the outside of the specific space 300a (so as not to be exposed to the specific space 300a).

Circuit Configuration for Determination of Passage of Object in Fourth Embodiment Next, the circuit configuration for determining the ejection state of the micro drop of the sample solution from the micropipette 100 (see FIG. 8) by using the structure in the fourth embodiment will be explained with reference to FIG. 16.

Figure 16:
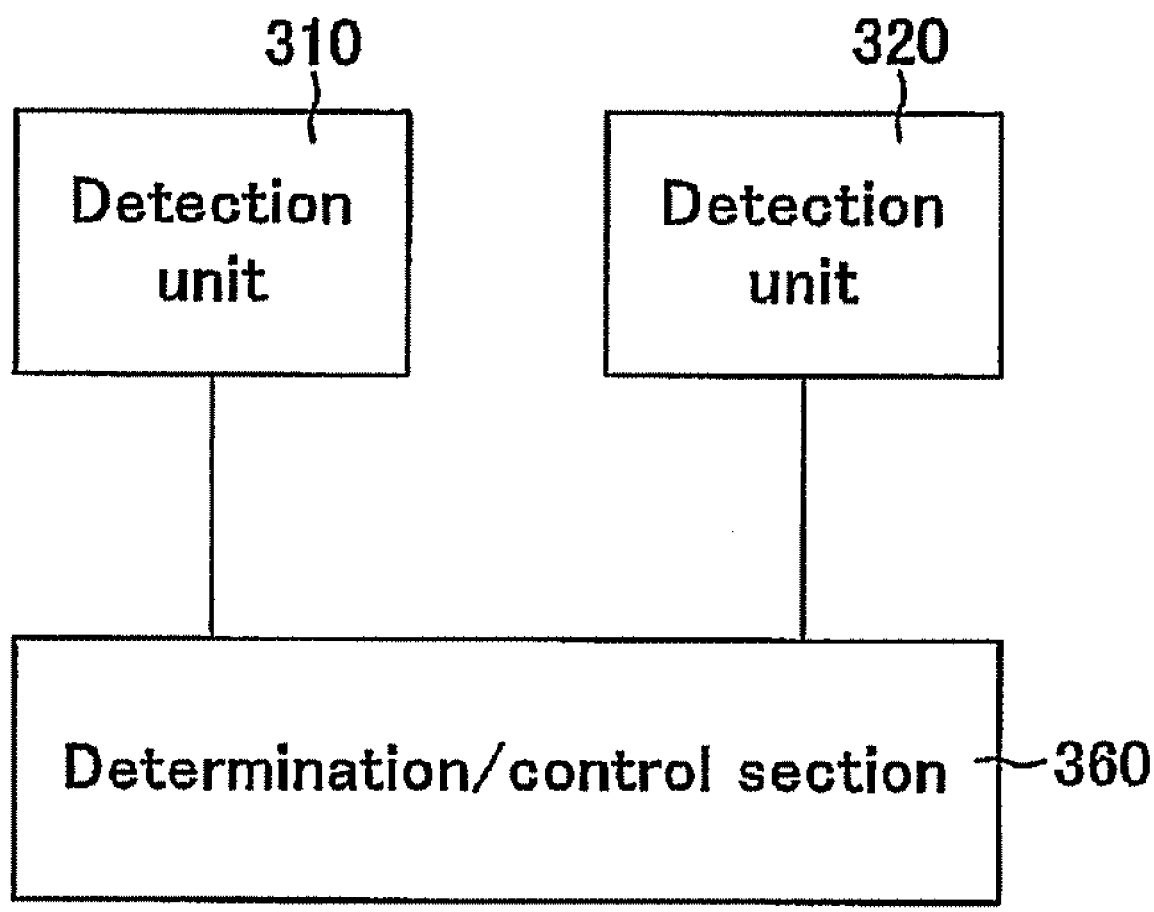
FIG. 16 is a block diagram schematically showing the electric circuit configuration applied to the passage detection apparatus according to the fourth embodiment shown in FIG. 15.

As shown in FIG. 16, the present embodiment employs a simple circuit configuration in which the detection units 310 and 320 are connected to the determination/control unit 360.

The determination/control unit 360 has a circuit configuration including the capacitor C1, voltmeter 312, and DC power supply PS in FIGS. 15A and 15B.

Description of Operation of Object Passage Determination in Fourth Embodiment According to the fourth embodiment shown in FIGS. 15A and 15B, the dielectric constant in the specific space 300a changes when the micro drop enters the specific space 300a. The change in the dielectric constant changes the electrostatic capacitance (or impedance) of the virtual capacitor C2 formed between the first electrode 311 and the second electrode 321. The value of the voltage acquired by the voltmeter 312 is changed by the change in the electrostatic capacitance. Whether the micro drop enters the specific space 300a or not and the size of the micro drop can be determined by the change in the voltage value.

In the structure shown in FIG. 15A, the first electrode 311 and the second electrode 321 are arranged to face the specific space 300a. According to this structure, the distance between the electrodes in the virtual capacitor C2 reduces, and the dielectric layer (first substrate 330 or the second substrate 340) is not interposed between the first electrode 311 and the second electrode 321. Therefore, even the passage of an extremely micro drop (e.g., picoliter order) can be detected with high sensitivity.

In the structure shown in FIG. 15B, the first electrode 311 and the second electrode 321 are arranged at the outside of the specific space 300a (so as not to be exposed to the specific space 300a). Specifically, the inner wall surface of the specific space 300a is made of the surface of the dielectric member. According to the structure described above, the occurrence of fault (short-circuit between electrodes or corrosion) on the first electrode 311 and the second electrode 321 due to the deposition of the micro drop can be prevented. Consequently, the passage state of the sample solutions having various properties in the specific space 300a can be satisfactorily detected.

Embodiment 5

Figure 17:
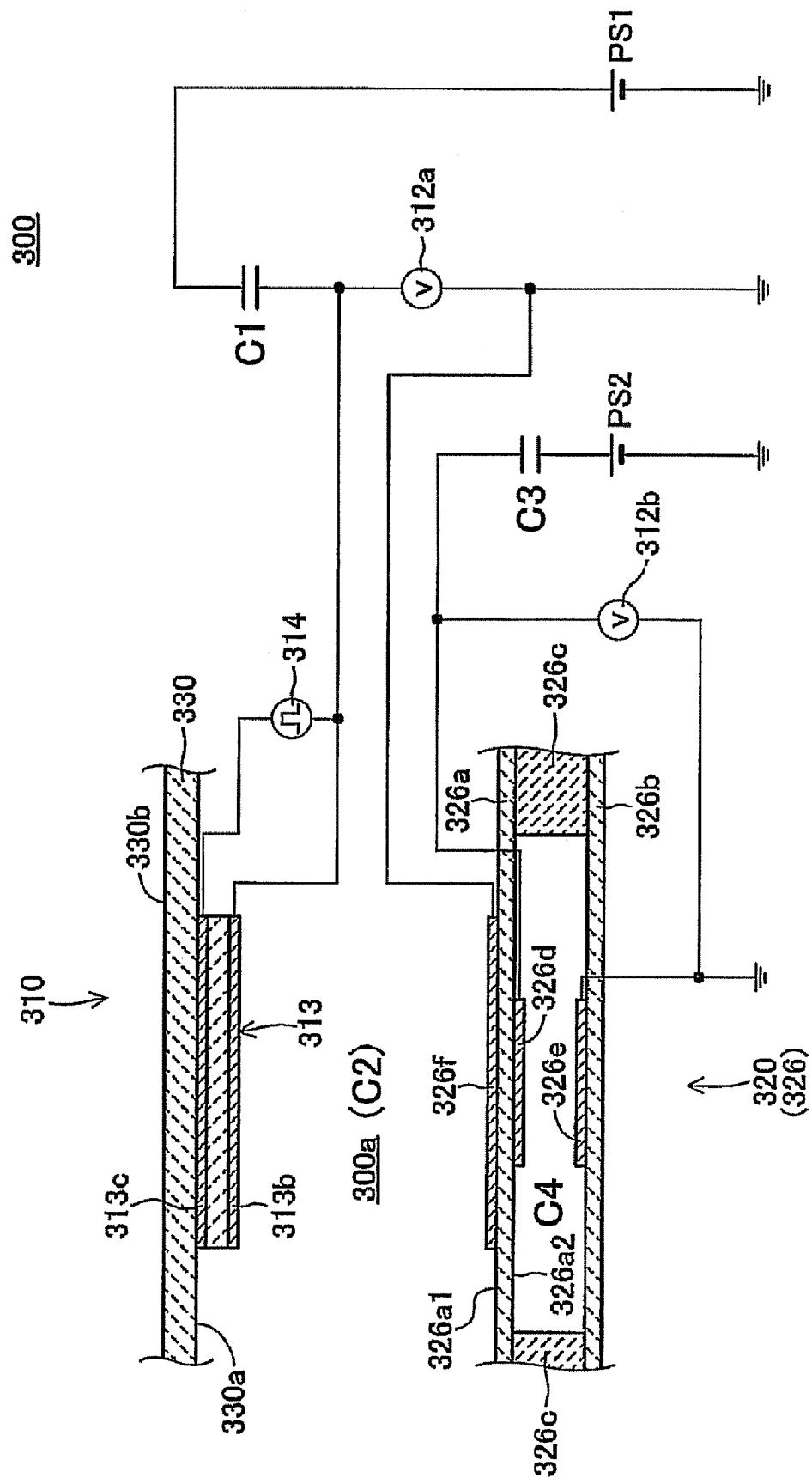
FIG. 17 is an enlarged sectional view showing the fifth embodiment of the passage detection apparatus shown in FIG. 9.

FIG. 17 is an enlarged sectional view showing the structure of the detection units 310 and 320 according to the fifth embodiment. The passage detection apparatus 300 according to the present embodiment has a structure in which the second embodiment shown in FIG. 13 and the third embodiment shown in FIG. 14 are combined. Specifically, the passage detection apparatus 300 according to the present embodiment is configured to determine whether or not the micro drop of the sample solution passes through the specific space 300a or the volume of the micro drop on the basis of the change in the electrostatic capacitance in the specific space 300a and the propagation state of the ultrasonic wave in the specific space 300a, like the second embodiment shown in FIG. 13. The structure in the present embodiment is the same as the structure of the second embodiment except that an electrostatic microphone 326 is used as the detection unit 320 instead of the second piezoelectric/electrostrictive element 323 (see FIG. 13) and the electric circuit configuration involved with the electrostatic microphone 326 is slightly different from that in the second embodiment.

Specifically, the first piezoelectric/electrostrictive element 313 is arranged such that the drive electrode 313b is positioned at the side of the specific space 300a. The drive electrode 313b is connected to the DC power supply PS through a known capacitor C1 having an electrostatic capacitance.

The pulse generating source 314 is connected to the drive electrode 313b and the first reference electrode 313c.

The electrostatic microphone 326 in the present embodiment has a vibration plate 326a, support plate 326b, spacer 326c, first detection electrode 326d, and second detection electrode 326e, those of which are the same as the vibration plate 325a, support plate 325b, spacer 325c, first detection electrode 325d, and second detection electrode 325e of the electrostatic microphone 325 in FIG. 14, and further has a second electrode 326f. The second electrode 326f is formed on the inner surface 326f/1 of the vibration plate 326a. The first detection electrode 326d is connected to a DC power supply PS2 through a known capacitor C3 having an electrostatic capacitance. The second detection electrode 326e is grounded.

The second electrode 326f of the electrostatic microphone 326 and the drive electrode 313b of the first piezoelectric/electrostrictive element 313 are arranged so as to face the specific space 300a, and they are connected to the voltmeter 312a. The first detection electrode 325d and the second detection electrode 325e are connected to the voltmeter 312b.

As described above, the passage detection apparatus 300 in the present embodiment is configured to determine whether or not the micro drop of the sample solution passes through the specific space 300a and the volume of the micro drop on the basis of the change in the partial voltage of the virtual capacitor C2 in the serial circuit of the known capacitor C1 and the virtual capacitor C2, and the change in the partial voltage of the virtual capacitor C4 in the serial circuit formed by the known capacitor C3 and the virtual capacitor C4 formed by the electrostatic microphone 326.

Description of Operation of Object Passage
Determination in Fifth Embodiment

In the structure of the present embodiment, the drive control of the first piezoelectric/electrostrictive element 313, etc. and the passage of the micro object or the like can be determined as shown in FIG. 12 by using the circuit configuration shown in FIG. 11.

Referring to FIG. 17, according to the structure of the fifth embodiment, when the first piezoelectric/electrostrictive element 313 constituting the detection unit 310 is driven at a predetermined timing, ultrasonic wave is generated like the second embodiment. This ultrasonic wave propagates through the medium in the specific space 300a to reach the vibration plate 326a. Accordingly, the vibration plate 326a is vibrated. By the vibration of the vibration plate 326a, the distance of the gap between the first detection electrode 326d and the second detection electrode 326e changes (i.e., the electrostatic capacitance of the capacitor C4 changes). With the change of the electrostatic capacitance of the virtual capacitor C4, the partial voltage generated at both ends of the virtual capacitor C4 in the serial circuit made by the virtual capacitor C4 and the known capacitor C3 changes. Specifically, the voltage generated at the electrostatic microphone 326 changes. The voltage generated at the electrostatic microphone 326 is acquired by the voltmeter 312b.

According to the present embodiment, the change in the partial voltage of the virtual capacitor C2, which is formed between the drive electrode 313b of the first piezoelectric/electrostrictive element 313 and the second electrode 326f of the electrostatic microphone 326 is acquired by the voltmeter 312a, like the aforesaid second embodiment. Whether the micro object of the sample solution passes through the specific space 300a or not or the volume of the micro object can be determined on the basis of the output from the voltmeters 312a and 312b. For example, when an appropriate statistical process is carried out by the determination/control section 360 in FIG. 11 to the result of the detection on the basis of the output from the voltmeter 312a and the result of the detection on the basis of the voltmeter 312b, the passage of the object can be detected with higher reliability, regardless of the property of the object (size, chargeability, etc.).

<Suggestion of Modifications>

The above-described embodiment has been disclosed merely to illustrate representative embodiment of the present invention considered as the most preferred embodiments at the time of filing of the present application. Consequently, the present invention is not limited to the above-described embodiments, and it is appreciated that various modifications are possible without changing essential parts of the present invention.

Hereinafter, a few modifications will be illustrated within the limits of addition possible at the time of filing of the present application (as far as time is allowed) under the first-to-file rule. However, it is not necessary to mention that the present invention is also not limited to these modifications. Limiting the present invention based on the disclosures of the embodiments described above and the modifications described below (especially, limiting the respective components constituting the means to solve the problems of the present invention, particularly, the components which are expressed operatively and functionally, based on the description of the preferred embodiments) is not allowed because the limitation trespasses on benefits of the applicant who has hastened to file the application under the first-to-file rule, the limitation provides imitators with undue profits, and therefore, the limitation is opposed to the purpose of the patent law prescribing the protection and utilization of the invention. Furthermore, it is not necessary to mention that the following modifications can be appropriately combined with each other within the scope of consistency.

(i) The present invention is not limited to the micropipettes disclosed in the above-described embodiment. Also, the flight direction of the micro object is not limited to the vertically-downward direction. As the vibration used for the passage detection, sound wave or heat can be utilized in addition to ultrasonic wave. Further, there is no limitation on the medium through which the micro object passes. For example, the present invention is preferably applicable even in case where various gases in addition to air, or liquid such as water, oil, etc. are used as the medium.

(ii) The manner of mounting the first piezoelectric/electrostrictive element 313 to the first substrate 330 and the manner of mounting the second piezoelectric/electrostrictive element 323 to the second substrate 340 in FIGS. 10A and 10B can be modified to the manner other than the manner illustrated in the figure. For example, one of the first piezoelectric/electrostrictive element 313 and the second piezoelectric/electrostrictive element 323 may be arranged to face the specific space 300a, and the other may be arranged at the outside of the specific space 300a. Further, the first piezoelectric/electrostrictive element 313 may be arranged such that the drive electrode 313b faces the specific space 300a. Alternatively, the second piezoelectric/electrostrictive element 323 may be arranged such that the signal output electrode 323 faces the specific space 300a.

(iii) In FIG. 13, the first piezoelectric/electrostrictive element 313 may be arranged on the outer surface 330b. The second piezoelectric/electrostrictive element 323 may be arranged on the outer surface 340b.

(iv) The known capacitors C1 and C3 in FIGS. 13 to 15 and 17 can be replaced by a resister. An optional circuit configuration may be employed for the circuit configuration in each of the above-mentioned figures.

(v) The manner other than the illustrated one can be employed for the manner of mounting the first piezoelectric/electrostrictive element 313 to the first substrate 330 in FIG. 14. For example, the first piezoelectric/electrostrictive element 313 may be arranged on the outer surface 330b. Further, the first piezoelectric/electrostrictive element 313 may be arranged such that the first reference electrode 313c faces the specific space 300a.

(vi) The vibration plate 325a and the support plate 325b in FIG. 14 may be made of a conductive material. By virtue of this structure, the functions of the first detection electrode 325d and the second detection electrode 325e may be provided to the vibration plate 325a and the support plate 325b.

(vii) The width of the specific space 300a in FIGS. 14 to 17 can also configured to satisfy the above-mentioned equation.

(viii) In FIG. 17, the first piezoelectric/electrostrictive element 313 may be arranged on the outer surface 330b.

(ix) In FIG. 17, the first detection electrode 326d and the voltmeter 312a may be connected to each other, whereby the second electrode 326f may be omitted. Specifically, the electrostatic microphone 326 may be configured in such a manner that the first detection electrode 326d has the function same as that of the second electrode 321 in FIGS. 15A and 15B. In particular, the first piezoelectric/electrostrictive element 313 is arranged on the outer surface 330b, and the above-mentioned configuration of omitting the second electrode 326f is employed, whereby the configuration in which the inner surfaces 330a and 326a1 of the first substrate 330 and the vibration plate 326a (second substrate) face the specific space 300a can be realized. In this case, the vibration plate 326a and the support plate 326b may be made of a conductive material. By virtue of this structure, the function of the first detection electrode 326d and function of the second detection electrode 326e can be provided to the vibration plate 326a and the support plate 326b.

Figure 18:
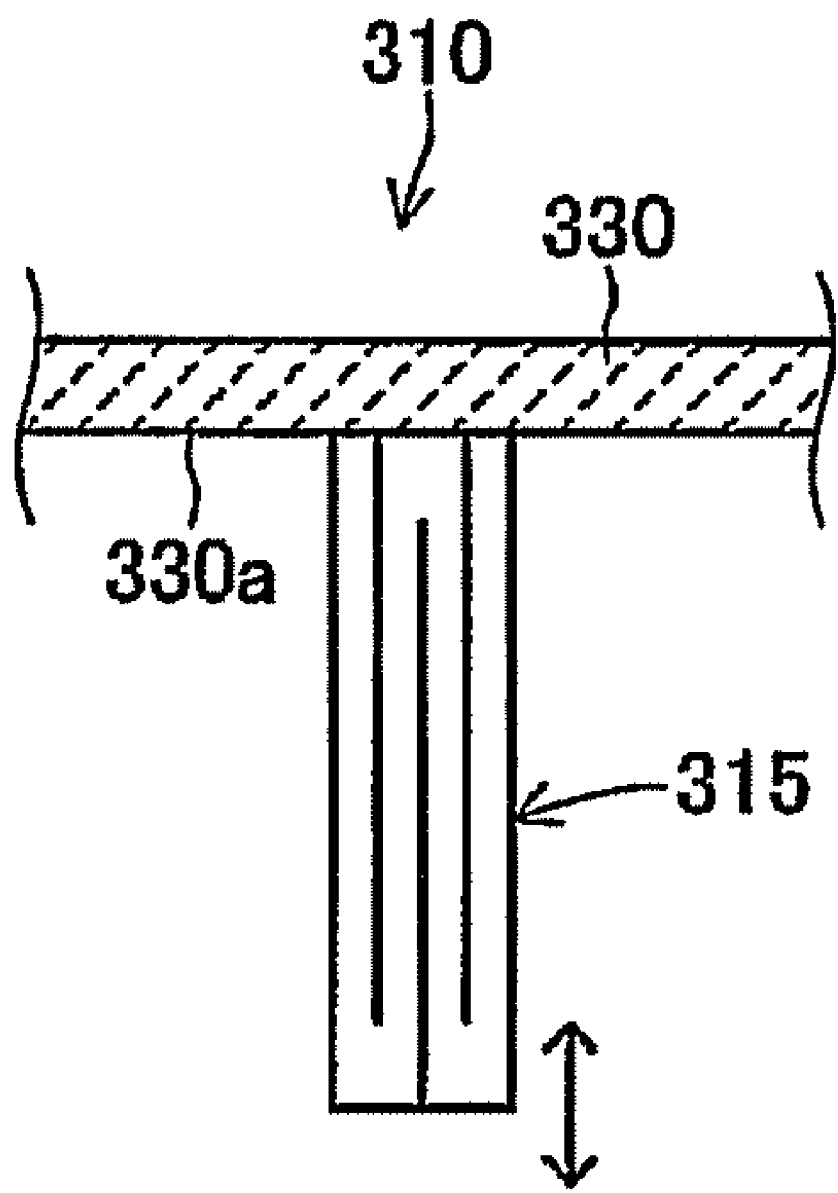
FIG. 18 is an enlarged sectional view showing the modification of the detection unit, serving as the vibration transmitting source, in the passage detection apparatus shown in FIG. 10 to FIG. 17.

(x) A multi-layer piezoelectric/electrostrictive element 315 shown in FIG. 18 may be employed as the piezoelectric/electrostrictive element 313 constituting the detection unit 310 serving as the vibration generating source in FIGS. 10 to 17. Accordingly, the intensity of the generated ultrasonic wave is enhanced, so that the passage can be detected with enhanced sensitivity.

In this case, as illustrated in FIG. 19, the detection unit 310 serving as the vibration generating source and the detection unit 320 for reception have the different structure. With this structure, the primary resonance frequencies of the detection unit 310 serving as the vibration generating source and the detection unit 320 for the reception are equal to each other, but the high-order resonance frequencies are different from each other.

In this configuration, the output from the detection unit 320 for the reception on the basis of the vibration other than the desired vibration mode in the detection unit 310 for the transmission is suppressed. Therefore, the S/N ratio in detecting the passage of an object is enhanced. Accordingly, a detection of a more micro object becomes possible with this configuration.

Figure 20:
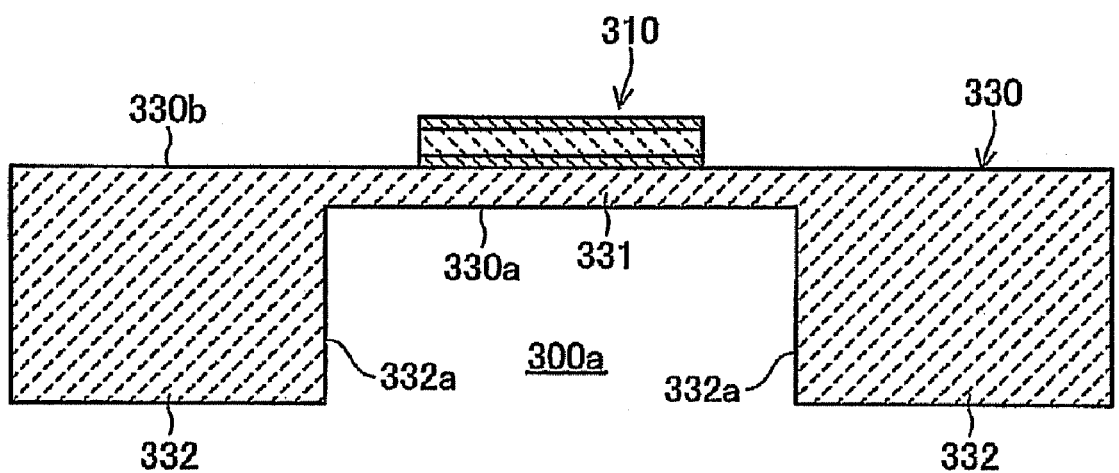
FIG. 20 is an enlarged sectional view showing the modification of the first substrate shown in FIG. 9.

(xi) The structure shown in FIG. 20 can be employed as the structure of the first substrate 330 that supports the detection unit 310. In FIG. 20, a piezoelectric/electrostrictive element is illustrated as an example of the structure of the detection unit 310. It is to be noted that the specific structure of the detection unit 310 is not limited in the explanation of the modification.

In this modification, the first substrate 330 has a plate-like thin vibration plate 331, and plate-like thick support plate 332 formed at both sides of the thin vibration plate 331, wherein the thin vibration plate 331 and the thick support plate 332 are integrally formed. The thick support plate 332 is made of a material same as the material of the thin vibration plate 331, and formed to be thicker than the thin vibration plate 331. The detection unit 310 is attached to the thin vibration plate 331.

According to this structure, the first substrate 330 is configured such that the thin vibration plate 331 is bridged between the adjacent thick support plates 332. Therefore, the vibration can be generated from the detection unit 310, serving as the vibration generating source, with high output.

As shown in FIG. 20, the outer surface 330b of the first substrate 330 in the present modification is made of the outer surfaces of the thin vibration plate 331 and the thick support plates 332. Specifically, the first substrate 330 in the present modification is configured such that the outer surface of the thin vibration plate 331 and the outer surface of the thick support plate 332 are continuous on the same plane. The first substrate 330 is configured such that the space enclosed by the inner surface 330 of the first substrate, which is made of the inner surface of the thin vibration plate 331, and the side face 332a of the thick support plate 332 (the space at the inside of the concave portion formed at the side of the inner surface 330a of the first substrate 330) is included in the specific space 300a.

According to this structure, the above-mentioned concave portion composing the specific space 300a is formed at the side of the inner surface 330a of the first substrate 330. Therefore, a part of the specific space 300a can be formed in the range of the thickness of the first substrate 330. Accordingly, the passage detection apparatus can be miniaturized.

The side face 332a of the thick support plate 332 shown in FIG. 20 may be configured to be capable of reflecting sound wave or ultrasonic wave.

According to the above-mentioned structure, sound wave or ultrasonic wave can be reflected with high efficiency by the side face 332a of the thick support plate 332, which constitutes the inner wall surface of the above-mentioned concave portion composing the specific space 300a. Therefore, the directivity when the sound wave or ultrasonic wave propagates through the medium in the specific space 300a is enhanced. Consequently, the passage can satisfactorily be detected even though the output of the detection unit 310 constituting the vibration generating source is reduced to reduce the power consumption.

Although it is illustrated in FIG. 20 as if the detection unit 310 is attached to the outer surface 330b of the first substrate 330 (thin vibration plate 331), the present modification is not limited thereto. Specifically, the detection unit 310 may be attached to the inner surface 330a of the first substrate 330 (thin vibration plate 331).

Figure 21:
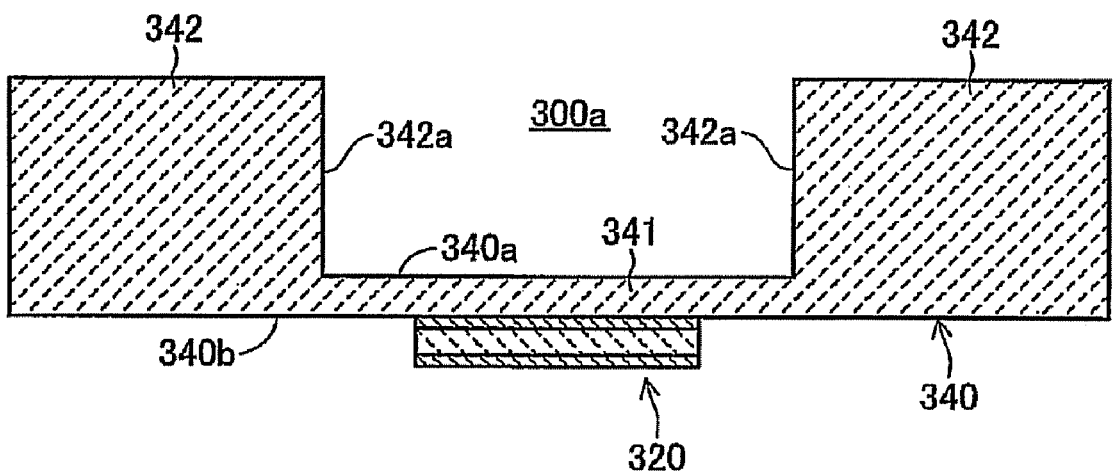
FIG. 21 is an enlarged sectional view showing the modification of the second substrate shown in FIG. 9.

(xii) The structure shown in FIG. 21 can be applied as the structure of the second substrate 340 for supporting the detection unit 320. It is to be noted that FIG. 21 shows the piezoelectric/electrostrictive element as one example of the structure of the detection unit 320, but the specific structure of the detection unit 320 is not limited in the explanation of the present modification (for example, the electrostatic microphone 325 in FIG. 14 or the electrostatic microphone 326 in FIG. 17 can be employed).

In the present modification, the second substrate 340 has a plate-like thin vibration plate 341, and plate-like thick support plates 342 formed at both sides of the thin vibration plate 341, wherein the thin vibration plate 341 and the thick support plate 342 are integrally Donned. The thick support plate 342 is made of a material same as the material of the thin vibration plate 341, and formed to be thicker than the thin vibration plate 341. The detection unit 320 is attached to the thin vibration plate 341.

According to this structure, the second substrate 340 according to this modification is configured such that the thin vibration plate 341 is bridged between the adjacent thick support plates 342. Therefore, the thin vibration plate 341 can be vibrated with high efficiency by the vibration propagated through the medium in the specific space 300*a*. Accordingly, the detection unit 320 receives the vibration with high sensitivity, whereby the passage or the like of the object can be detected with high sensitivity.

As shown in FIG. 21, the outer surface 340*b* of the second substrate 340 in the present modification is made of the outer surfaces of the thin vibration plate 341 and the thick support plates 342. Specifically, the second substrate 340 in the present modification is configured such that the outer surface of the thin vibration plate 341 and the outer surface of the thick support plate 342 are continuous on the same plane. The second substrate 340 is configured such that the space enclosed by the inner surface 340*a* of the second substrate, which is made of the inner surface of the thin vibration plate 341, and the side face 342*a* of the thick support plate 342 (the space at the inside of the concave portion formed at the side of the inner surface 340*a* of the second substrate 340) is included in the specific space 300*a*.

According to this structure, the above-mentioned concave portion composing the specific space 300*a* is formed at the side of the inner surface 340*a* of the second substrate 340. Therefore, a part of the specific space 300*a* can be formed in the range of the thickness of the second substrate 340. Accordingly, the passage detection apparatus can be miniaturized.

The side face 342*a* of the thick support plate 342 shown in FIG. 21 may be configured to be capable of reflecting sound wave or ultrasonic wave.

According to the above-mentioned structure, sound wave or ultrasonic wave can be reflected with high efficiency by the side face 342*a* of the thick support plate 342, which constitutes the inner wall surface of the above-mentioned concave portion composing the specific space 300*a*. Therefore, the directivity when the sound wave or ultrasonic wave propagates through the medium in the specific space 300*a* is enhanced. Consequently, the passage can satisfactorily be detected even though the output of the detection unit 320 is reduced to reduce the power consumption.

Although it is illustrated in FIG. 21 as if the detection unit 320 is attached to the outer surface 340*b* of the second substrate 340 (thin vibration plate 341), the present modification is not limited thereto. Specifically, the detection unit 320 may be attached to the inner surface 340*a* of the second substrate 340 (thin vibration plate 341).

Figure 22:
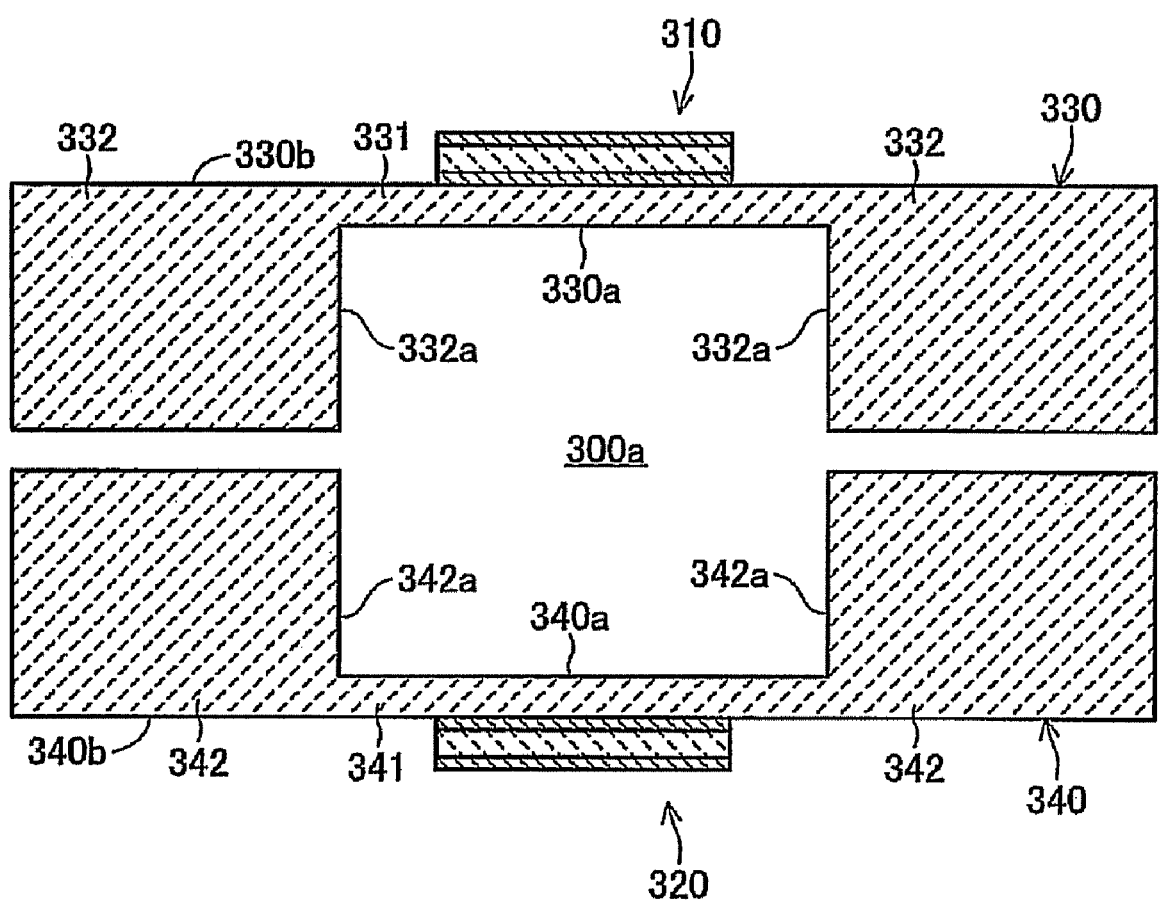
FIG. 22 is an enlarged sectional view showing an example of the structure of the passage detection apparatus having the first substrate shown in FIG. 21 and the second substrate shown in FIG. 22.

(xiii) As shown in FIG. 22, the first substrate 330 and the second substrate 340 may be configured as illustrated in FIGS. 20 and 21. In the structure described above, the specific space 300*a* is substantially formed by the space enclosed by the inner surface 330*a* of the thin vibration plate 331 at the first substrate 330, the side face 332*a* of the thick support plate 332 at the first substrate 330, the inner surface 340*a* of the thin vibration plate 341 at the second substrate 340, and the side face 342*a* of the thick support plate 342 at the second substrate 340.

According to the structure described above, nearly entire specific space 300*a* can be formed within the range of the thickness obtained by superimposing the first substrate 330 and the second substrate 340. Therefore, the passage detection apparatus can further be miniaturized.

The side face 332*a* of the thick support plate 332 at the first substrate 330 and the side face 342*a* of the thick support plate 342 at the second substrate 340 may be configured to be smooth to an extent of being capable of nearly totally reflecting sound wave or ultrasonic wave. With this structure, the passage can be detected with enhanced sensitivity by a simplified structure.

Figure 23A:
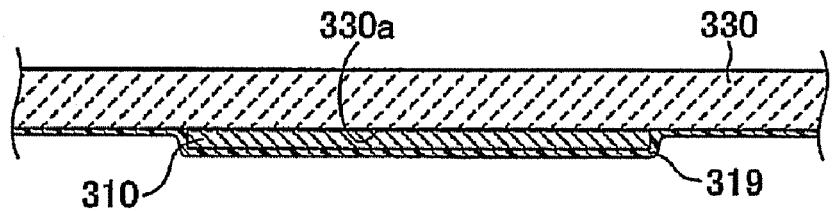
FIGS. 23A and 23B are enlarged sectional views showing other modifications of the detection unit, serving as the vibration transmitting source, shown in FIGS. 10 to 22.
Figure 23B:
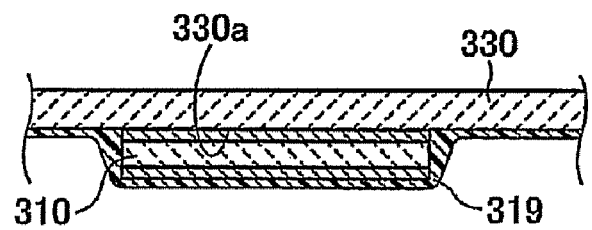

(xiv) When the detection unit 310 is provided on the inner surface 330*a* of the first substrate 330, it is preferable that an insulating coating layer 319 that covers the detection unit 310 is formed on the inner surface 330*a* as shown in FIGS. 23A and 23B. By virtue of this structure, it is prevented that the detection unit 310 is attacked, even though the sample solution is corrosive or conductive, whereby the passage of the object and/or the size of the object can satisfactorily be determined.

Figure 23C:
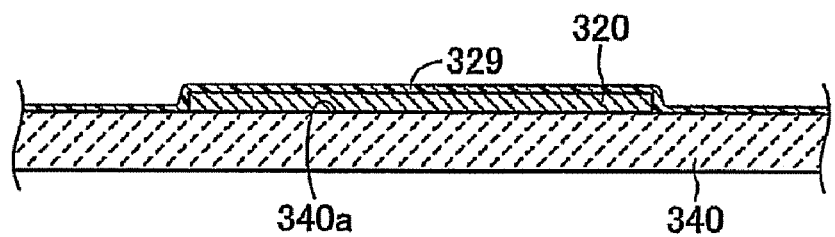
FIGS. 23C and 23D are enlarged sectional views showing other modifications of the detection unit at the reception side shown in FIGS. 10 to 22.
Figure 23D:
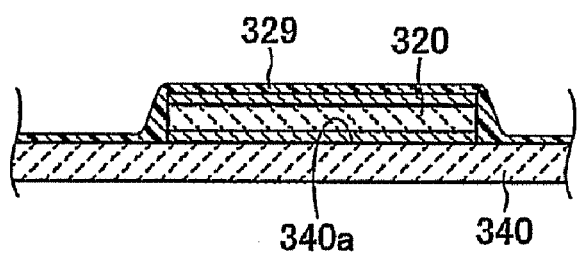

Similarly, when the detection unit 320 is provided on the inner surface 340*a* of the second substrate 340, it is preferable that an insulating coating layer 329 that covers the detection unit 320 is formed on the inner surface 340*a* as shown in FIGS. 23C and 23D.

(xv) A piezoelectric polymer film can be used as the detection unit 320. Accordingly, very small sound wave (ultrasonic wave) can be detected, so that the sensitivity in detecting the passage of the object can be enhanced.

(xvi) In the aforesaid embodiments, the width L of the specific space 300*a* is set so as to satisfy the following equation, supposing that the wavelength of the vibration propagating through the medium (air, etc.) in the specific space 300*a* is $\lambda$, and n is a natural number.

$$L = n\lambda$$

It is to be noted that, instead of the above-mentioned structure, the width L may be set so as to satisfy the following equation, supposing that m is a natural number.

$$L = (m/2) \cdot \lambda$$

Figure 24:
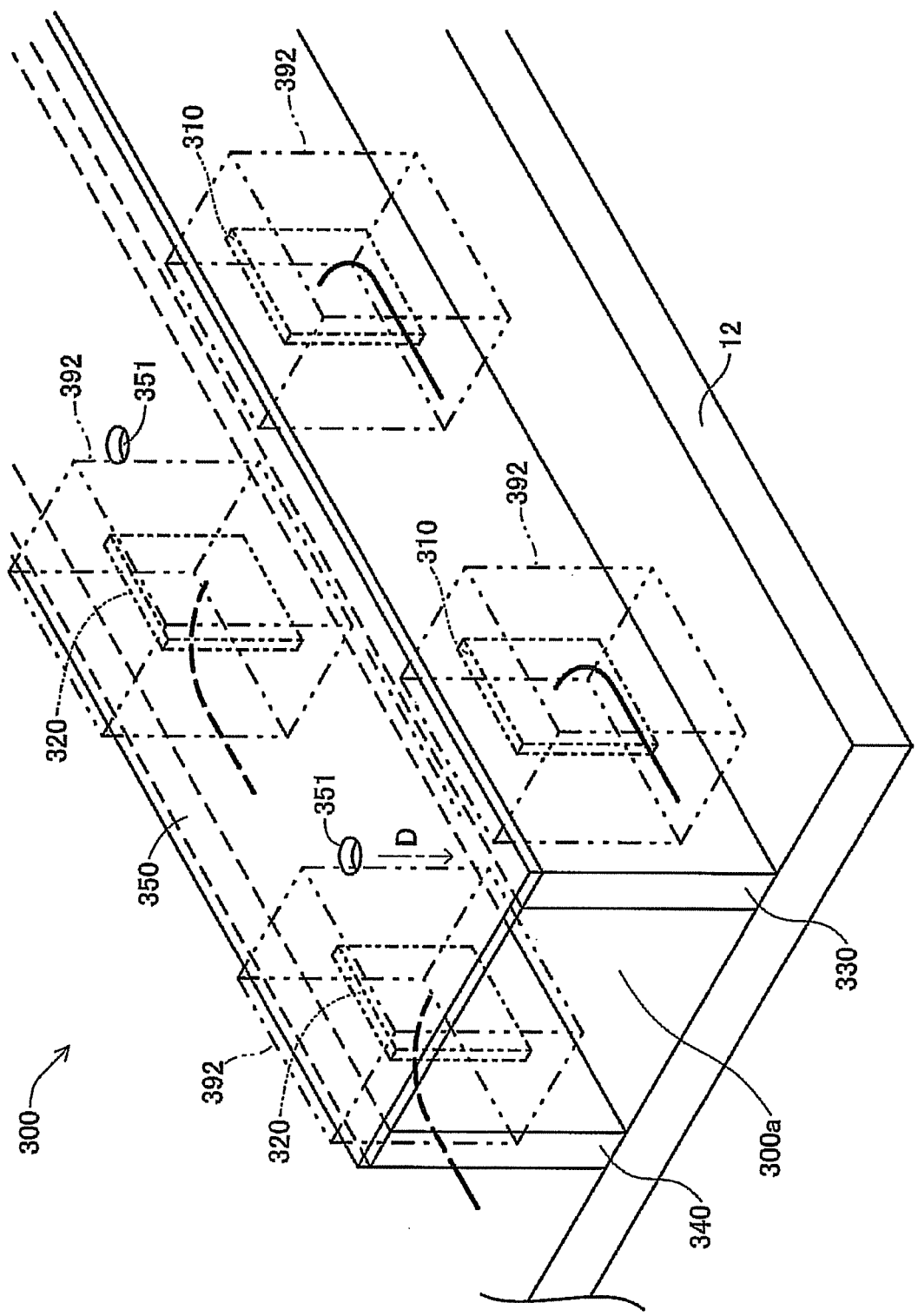
FIG. 24 is an enlarged perspective view showing another modification of the passage detection apparatus shown in FIG. 9.

(xvii) As shown in FIG. 24, an element noise reducing shield member 392 may be provided. The element noise reducing shield member 392 is provided in such a manner that the element portions (the first piezoelectric/electrostrictive element 313 or the second piezoelectric/electrostrictive element 323, etc.) for transmission and reception at the detection unit 310 and the detection unit 320 are opposite to each other and the portion other than the element portions are covered in all directions.

Figure 25:
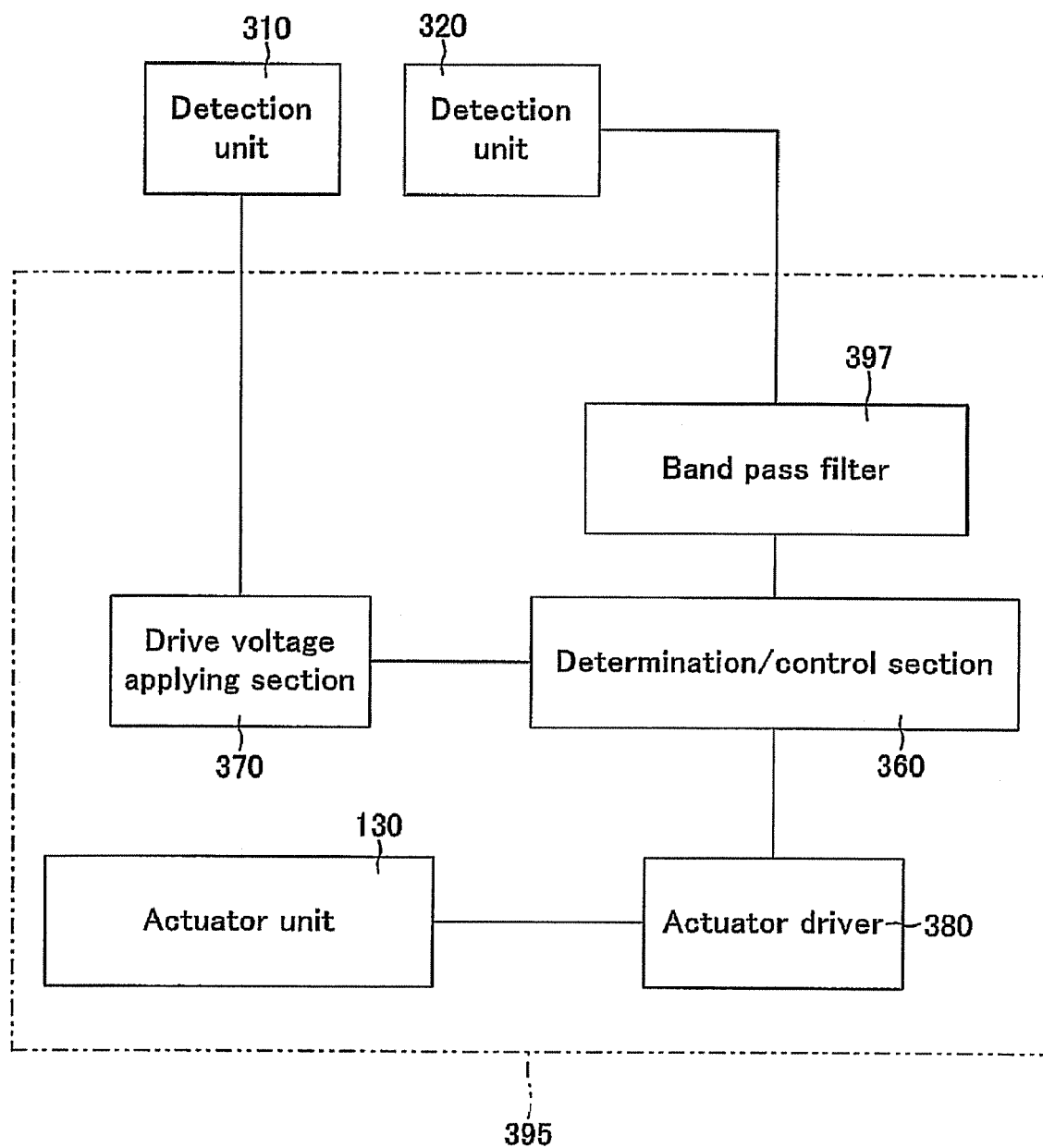
FIG. 25 is a block diagram showing the modification of an electric circuit configuration applied to the passage detection apparatus according to the embodiments shown in FIGS. 11 to 16.

As shown in FIG. 25, a circuit noise reducing shield member 395 may be provided. The circuit noise reducing shield member 395 is configured to cover the electric circuit such as the determination/control section 360, etc. for eliminating electrical noise exerted on the electric circuit.

In the structure described above, electrical noise is eliminated. Therefore, S/N ratio in the detection of the passage of the object is enhanced. Accordingly, a more micro object can be detected with high precision by the structure described above.

Increasing sensitivity achieved by the reduction of noise can be realized by employing at least any one of the element noise reducing shield member 392 that covers the detection unit 310, the element noise reducing shield member 392 that covers the detection unit 320, and the circuit noise reducing shield member 395. It suffices that the circuit noise reducing shield member 395 shields at least the determination/control section 360.

(xviii) As shown in FIG. 25, a band pass filter 397 may be provided in the circuit configuration as the determination unit. The band pass filter 397 is interposed between the detection unit 320 and the determination/control unit 360. The band pass filter 397 is configured to limit the frequency of the output at the detection unit 320 to the band around the desired resonance frequency (specifically, within the range of ±10% of the desired resonance frequency, for example).

In the structure described above, a mechanical noise is eliminated that is based upon ambient sound wave or the vibration or the like of an unnecessary mode other than the vibration of the desired mode corresponding to the desired resonant frequency. Accordingly, the S/N ratio for the detection of the passage of the object is enhanced. Consequently, an object having more micro size can be detected with high precision.

The band pass filter 397 can be provided in the determination/control section 360.

Figure 26:
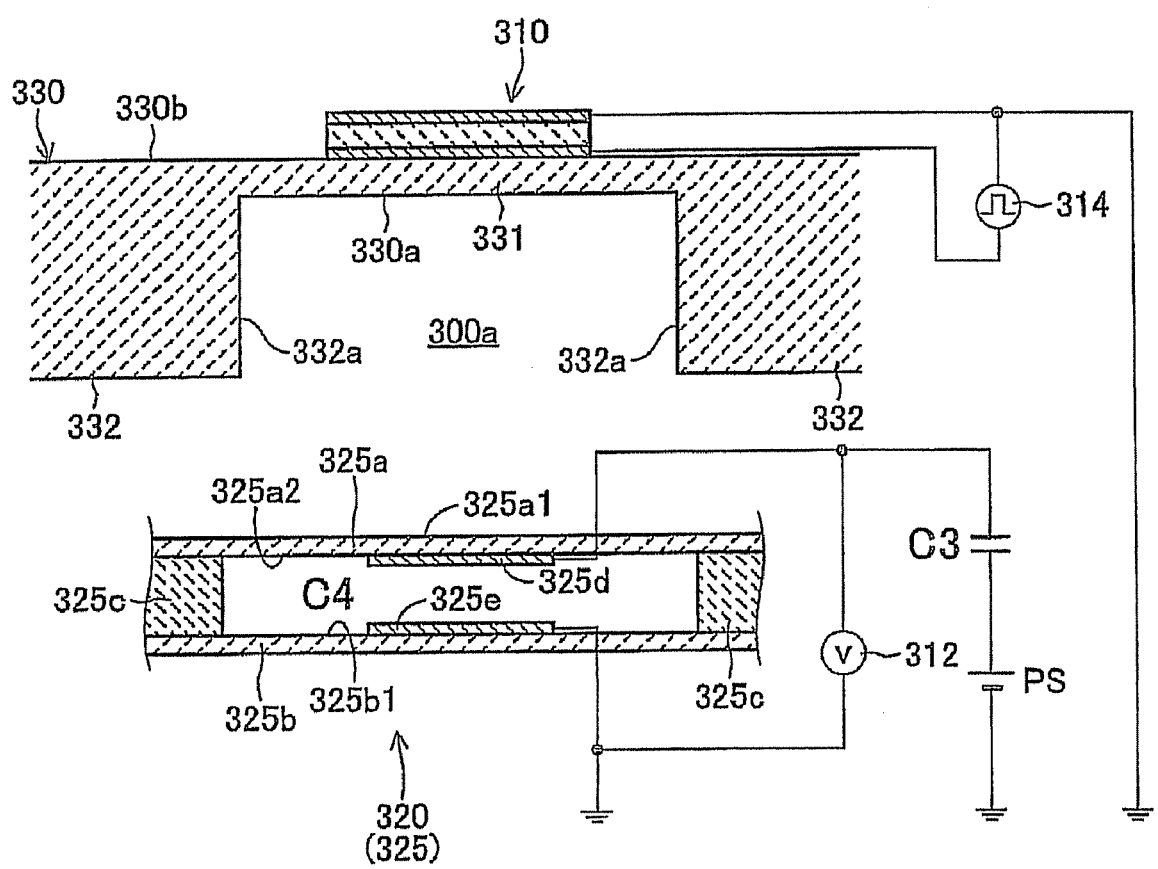
FIG. 26 is an enlarged sectional view showing an example of the structure of the passage detection apparatus having the first substrate as shown in FIG. 20 and the second detection unit as shown in FIG. 14.

(xxiv) As shown in FIG. 26, the first substrate 330 and the first detection unit 310 may be configured as illustrated in FIG. 20 and the second detection unit 320 may be configured as illustrated in FIG. 14. In the structure described above, the specific space 300a is substantially formed by the space enclosed by the inner surface 330a of the thin vibration plate 331 at the first substrate 330, the side face 332a of the thick support plate 332 at the first substrate and the vibration plate 325a of the electrostatic microphone 325 used as the second detection unit 320.

The vibration plate 325a is made of a dielectric layer having a thin plate shape, and is a member for constituting the outer wall enclosing the specific space 300a. Specifically, the inner surface of the electrostatic microphone 325 facing the specific space 300a is made of the inner surface 325a1 of the vibration plate 325a. The support plate 325b is made of a dielectric layer having a thin plate shape. The support plate 325b is arranged so as to be parallel to the vibration plate 325a with a predetermined gap. The spacer 325c is a plate-like member formed with multiple through-holes, and is arranged between the vibration plate 325a and the support plate 325b so as to form a predetermined gap between the vibration plate 325a and the support plate 325b by the through-holes.

The first detection electrode 325d is formed on the outer surface 325a2, which is the backside of the inner surface 325a1, of the vibration plate 325a. The first detection electrode 325d is connected to the DC power supply PS through a known capacitor C3 having electrostatic capacitance. The second detection electrode 325e is formed on the inner surface 325b1, which faces the vibration plate 325a, of the support plate 325b, and arranged parallel to the first detection electrode 325d. The second detection electrode 325e is grounded. The first detection electrode 325d and the second detection electrode 325e are connected to the voltmeter 312 so as to acquire the voltage between the first detection electrode 325d and the second detection electrode 325e.

According to the structure described above, the side face 332a of the thick support plate 332 at the first substrate 330 may be configured to be smooth to an extent of being capable of nearly totally reflecting sound wave or ultrasonic wave. With this structure, the passage can be detected with enhanced sensitivity by a simplified structure.

(xxv) In addition, the respective components constituting the means to solve the problems of the present invention, particularly, the components which are expressed operatively and functionally, include all structures that can be operatively and functionally realized in addition to the clearly defined structures disclosed in the above-described embodiments and modifications.

What is claimed:

1. A passage detection apparatus of an object that can detect a passage of an object in a specific space, comprising:
a vibration generating source comprising a first piezoelectric/electrostrictive element having a drive electrode and a first reference electrode formed on opposing sides of a first dielectric layer;
a sensor unit that is arranged at a position corresponding to the vibration generating source across the specific space, and configured to be capable of generating an output according to the vibration, which propagates through a medium in the specific space, from the vibration generating source the sensor unit comprising:
a vibration plate made of a plate-shaped dielectric layer and constitutes an outer wall enclosing the specific space;
a first detection electrode formed on the vibration plate;
a support plate arranged parallel to the vibration plate with a predetermined gap; and
a second detection electrode formed on an inner surface, which faces the vibration plate, of the support plate, and arranged parallel to the first detection electrode;
a determination unit that determines the passage of the object in the specific space on the basis of the output from the sensor unit, wherein the determination unit is configured to determine the passage of the object in the specific space on the basis of an electrostatic capacitance between the first detection electrode and the second detection electrode; and
a first substrate made of a plate-shaped dielectric layer for supporting the first piezoelectric/electrostrictive element,
wherein the specific space is formed by a space between an inner surface of the first substrate and an inner surface of the vibration plate;
wherein the first substrate has a plate-shaped thin part and a plate-shaped thick part that is formed at both sides of the thin part and is thicker than the thin part,
wherein the first substrate is formed such that an outer surface of the thin part and an outer surface of the thick part are continuous on a same plane,
wherein the first piezoelectric/electrostrictive element is attached to the thin part of the first substrate, and
wherein the specific space includes a space enclosed by an inner surface of the thin part at the first substrate and a side face of the thick part at the first substrate.

2. A passage detection apparatus of an object according to claim 1, wherein
the first substrate and the vibration plate are arranged in such a manner that the distance L between the inner surface of the first substrate and the inner surface of the vibration plate satisfies the equation of $L = n\lambda$ or $L = (m/2) \cdot \lambda$ wherein the wavelength of the vibration propagating through the medium is $\lambda$, and n and m are natural numbers.

* * * * *